United States Patent
Chaparian et al.

(10) Patent No.: US 8,586,552 B2
(45) Date of Patent: Nov. 19, 2013

(54) 4,6-SUBSTITUTED 2,5-DIDEOXYSTREPTAMINE AMINOGLYCOSIDE ANTIBIOTICS

(71) Applicant: SelectX Pharmaceuticals, Inc., Boston, MA (US)

(72) Inventors: Michael G. Chaparian, Washington Township, MI (US); Michael Brady, Haverhill, MA (US); Scott Moe, Sudbury, MA (US); Babu Rao Renikuntla, Shrewsbury, MA (US); Srinivas Gadthula, Dublin, OH (US); Srinivasarao Meneni, Shrewsbury, MA (US); Venkata Sai Prakash Chaturvedula, Alpharetta, GA (US)

(73) Assignee: SelectX Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 13/755,275

(22) Filed: Jan. 31, 2013

(65) Prior Publication Data

US 2013/0203693 A1 Aug. 8, 2013

Related U.S. Application Data

(60) Provisional application No. 61/594,663, filed on Feb. 3, 2012.

(51) Int. Cl.
*A61K 31/70* (2006.01)
*C07H 15/00* (2006.01)
*C07H 15/20* (2006.01)

(52) U.S. Cl.
USPC ............. 514/40; 514/41; 536/13.7; 536/13.8; 536/16.8

(58) Field of Classification Search
None
See application file for complete search history.

(56) References Cited

U.S. PATENT DOCUMENTS

2004/0058880 A1* 3/2004 Liang et al. .................... 514/36

FOREIGN PATENT DOCUMENTS

| WO | 2010/030690 | 3/2010 |
|---|---|---|
| WO | 2012/004684 | 1/2012 |

OTHER PUBLICATIONS

Revuelta et al. "NMR-Based Analysis of Aminoglycoside Recognition by the Resistance Enyme ANT(4'): The Pattern of OH/NH3 Substitution Determines the Preferred Antibiotic Binding Mode and is Critical for Drug Activation". J. Am. Chem. Society, 130, 5086-5103 (2008).
Dhondikubeer et al. "Antibacterial Activity of Amphiphilic Tobramycin". J. of Antibiotics, 65, 495-498 (2012).
Inouye et al. "Chemical Modification of Kanamycin". Chem. Pharm. Bull., 15(12), 1888-1895 (1967).
Mingeot-Leclercq "New Derivatives of Kanamycin B Obtained by Modifications and Substitutions in Position 6". 2. In Vitro and Computer-Aided Toxicological Evaluation with Respect to Interactions with Phosphatidylinositol. J. Med. Chem., 34, 1476-1482 (1991).
Bera et al. "Antibacterial Activity of Guanidinylated Neomycin B- and Kanamycin A-derived Amphiphilic Lipid Conjugates". J. Antimicrob. Chemother., 65, 1224-1227 (2010).
Van Schepdael et al. "New Derivatives of Kanamycin B Obtained by Modifications and Substitutions in Position 6". 1. Synthesis and Microbiological Evaluation. J. Med. Chem., 34, 1468-1475 (1991).
Van Schepdael et al. "New Derivatives of Kanamycin B Obtained by combined Modification in Positions 1 and 6". Synthesis, Microbiological Properties, and in Vitro and Computer-Aided Toxicological Evaluation, J. Med. Chem., 34, 1483-1492 (1991).
Search Report for corresponding International Patent Application No. PCT/US2013/024083 dated Apr. 18, 2013.

* cited by examiner

*Primary Examiner* — Traviss C McIntosh, III
(74) *Attorney, Agent, or Firm* — Heslin Rothenberg Farley & Mesiti P.C.

(57) ABSTRACT

Aminoglycoside antibiotics of the formula

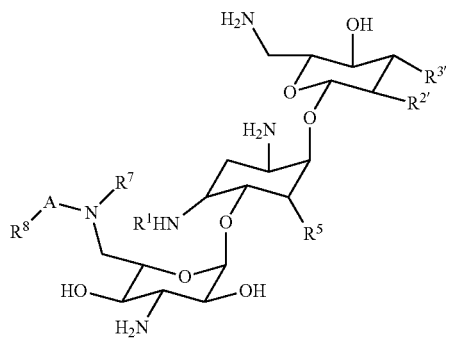

are disclosed. The compounds are useful for treating bacterial infections, particularly infections resistant to known antibiotics.

25 Claims, No Drawings

4,6-SUBSTITUTED 2,5-DIDEOXYSTREPTAMINE AMINOGLYCOSIDE ANTIBIOTICS

CROSS-REFERENCE TO RELATED APPLICATIONS

This application claims priority from U.S. provisional application 61/594,663, filed Feb. 3, 2012, the entire contents of which are incorporated herein by reference.

FIELD OF THE INVENTION

The invention relates to aminoglycoside antibiotics.

BACKGROUND OF THE INVENTION

Since their first clinical use with the introduction of streptomycin in 1947, the aminoglycosides (AG) have been one of the most important and widely used classes of antibiotics against most gram-negative and serious gram-positive infections. Aminoglycosides bind the A-site of the 30S ribosome, blocking bacterial protein synthesis through disruption of initiation and translation. AGs are actively transported into the bacterial cell by an energy-requiring process. Defective membrane proteins resulting from translational errors further enhance the activity of AGs by allowing passive entry of the antibiotic into the cell.

Over the past several decades of use, clinical resistance to the AGs has emerged. Aminoglycoside resistance generally occurs by one of several mechanisms, described here in order of clinical relevance:

1. Enzyme-mediated chemical modification of the drug by aminoglycoside modifying enzymes (AGME). These enzymes are carried and transferred easily by plasmids in clinical isolates and inactivate AGs by chemical modification resulting in greatly reduced ribosomal binding. Three general classes of AGME exist:
   a. N-Acetyltransferases (AAC)—catalyzes acetyl CoA-dependent acetylation of an amino group
   b. O-Adenyltransferases (ANT)—catalyzes ATP-dependent adenylation of hydroxyl group
   c. O-Phosphotransferases (APH)—catalyzes ATP-dependent phosphorylation of a hydroxyl group
2. Reduced uptake or decreased cell permeability. Most typically seen in *Pseudomonas aeruginosa* (Pae), this form of resistance is due to a transport defect resulting in broad, intermediate level resistance to all the AGs.
3. Efflux. Drugs are pumped out of the cell before they can cause cell death. This generally results in broad resistance to all AGs. AGs are affected by both general antibiotic efflux pumps and also by AG specific pumps.
4. Altered ribosome binding sites, typically by methylation, facilitated by 16S RNA methylases. Modification at the site of aminoglycoside interaction interferes with ribosomal binding. These enzymes are also plasmid mediated.

Coincident with the emergence of AG resistance is the rapid emergence of a variety of serious gram-negative infections, most notably hospital based (nosocomial) infections. Many of these infections are not susceptible to currently marketed and once effective antibiotics (aminoglycosides and beta-lactams) and thus pose a significant and urgent need for new or improved antibiotics. Aminoglycosides, having a long history of effective use against gram-negative infections such as Pae and *Klebsiella pneumoniae* (Kpn), seem well suited to address this problem if compounds can be created that effectively overcome the most clinically relevant mechanisms of AG resistance. In addition to overcoming resistance and increasing potency and spectrum, it is desirable to improve the therapeutic index, particularly by decreasing the nephrotoxicity and/or ototoxicity.

SUMMARY OF THE INVENTION

In one aspect the invention relates to compounds of formula I:

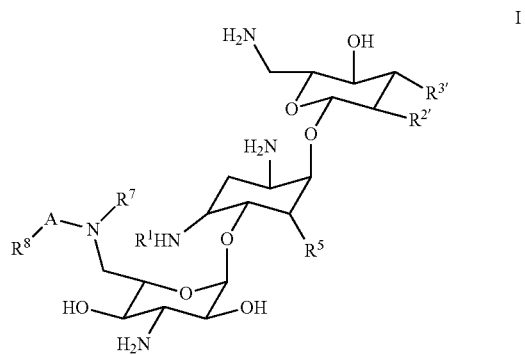

wherein
$R^{2'}$ is chosen from —OH and —NH$_2$;
$R^{3'}$ is chosen from H and —OH;
$R^1$ is chosen from H, —C(=NH)NH$_2$, and —C(=O)R$^{10}$, wherein
  $R^{10}$ is chosen from —(C$_1$-C$_{20}$)alkyl, —(C$_3$-C$_{10}$)carbocycle, —(C$_3$-C$_9$)heterocycle, —(C$_1$-C$_8$)alkyl(C$_3$-C$_{10}$)carbocycle, and —(C$_1$-C$_8$)alkyl(C$_3$-C$_9$)heterocycle wherein
    in said (C$_1$-C$_{20}$)alkyl or in the (C$_1$-C$_8$)alkyl portion of said (C$_1$-C$_8$)alkyl(C$_3$-C$_{10}$)carbocycle or (C$_1$-C$_8$)alkyl(C$_3$-C$_9$)heterocycle, one or two —CH— may be replaced with —N—, two —CH— may be replaced by —C=C—, and one or two —CH$_2$— may be replaced by —O—, —S—, —SO—, —SO$_2$—, —C≡C—, a (C$_3$-C$_{10}$)carbocycle or a (C$_3$-C$_6$)heterocycle and
    said (C$_1$-C$_{20}$)alkyl, (C$_3$-C$_{10}$)carbocycle, (C$_3$-C$_9$)heterocycle, (C$_1$-C$_8$)alkyl(C$_3$-C$_{10}$)carbocycle, (C$_1$-C$_8$)alkyl(C$_3$-C$_9$)heterocycle may be additionally substituted with from one to three substituents chosen independently from —CH$_3$, —OH, —NH$_2$, —COOH, =O, —NHCONH$_2$, —NHC(=NH)NH$_2$, —CN or halogen;
$R^5$ is chosen from H, halogen, N$_3$, —(C$_1$-C$_4$)alkynyl and —NHR$^{50}$, wherein R$^{50}$ is chosen from H, —(C$_3$-C$_{10}$)carbocycle, —(C$_3$-C$_9$)heterocycle, —(C$_1$-C$_8$)alkyl(C$_3$-C$_{10}$)carbocycle, —(C$_1$-C$_8$)alkyl(C$_3$-C$_9$)heterocycle and the deshydroxy residue of an aminoacid;
$R^7$ is chosen from H, —(C$_1$-C$_6$)alkyl and hydroxy-(C$_1$-C$_6$)alkyl;
$R^8$ is chosen from —(C$_1$-C$_{20}$)alkyl, —(C$_3$-C$_{10}$)carbocycle, —(C$_3$-C$_9$)heterocycle, —(C$_1$-C$_8$)alkyl(C$_3$-C$_{10}$)carbocycle, —(C$_1$-C$_8$)alkyl(C$_3$-C$_9$)heterocycle, —NR$^{80}$R$^{81}$, and —C(=NH)NH$_2$, wherein
  R$^{80}$ and R$^{81}$ are chosen independently from H and (C$_1$-C$_6$)alkyl;
  in said (C$_1$-C$_{20}$)alkyl or in the (C$_1$-C$_8$)alkyl portion of said (C$_1$-C$_8$)alkyl(C$_3$-C$_{10}$)carbocycle or (C$_1$-C$_8$)alkyl (C$_3$-C$_9$)heterocycle, one or two —CH— may be replaced with —N—, two —CH— may be replaced by —C=C—, and one or two —CH$_2$— may be replaced by —O—, —S—, —SO—, —SO$_2$—, —C≡C—, a (C$_3$-C$_{10}$)carbocycle or a (C$_3$-C$_6$)heterocycle; and said (C$_1$-C$_{20}$)alkyl, (C$_3$-C$_{10}$)carbocycle, (C$_3$-C$_9$)heterocycle, (C$_1$-C$_8$)alkyl(C$_3$-C$_{10}$)carbocycle, (C$_1$-C$_8$)alkyl(C$_3$-C$_9$)heterocycle may be additionally substituted with from one to three substituents chosen independently from —CH$_3$, —CH$_2$CH$_3$, —OH, —CH$_2$OH, —NH$_2$, —CH$_2$NH$_2$, —COOH, =O, —NHCONH$_2$, —NHC(=NH)NH$_2$, —CN and halogen;

or $R^7$ and $R^8$A, taken together with the nitrogen to which they are attached, form a (C$_3$-C$_9$)heterocycle, said (C$_3$-C$_9$) heterocycle optionally substituted with from one to three substituents chosen independently from —CH$_3$, —CH$_2$CH$_3$, —OH, —CH$_2$OH, —NH$_2$, —CH$_2$NH$_2$, —COOH, =O, —NHCONH$_2$, —NHC(=NH)NH$_2$, —CN and halogen; and A is chosen from a direct bond, —(C=O)—, —C(=O)O—, —NH(C=O)—, —(C=O)NH—, —NH(C=O)NH—, —(C=S)NH—, —NH(C=S)—, and —NH(C=S)NH—.

In another aspect, the invention relates to method of treating a mammal suffering from a bacterial infection, by administering a therapeutically effective amount of a compound described above.

In another aspect, the invention relates to pharmaceutical compositions comprising a pharmaceutically acceptable carrier and a compound described above.

DETAILED DESCRIPTION OF THE INVENTION

In one embodiment, the invention relates to a compound of the formula (I) shown below:

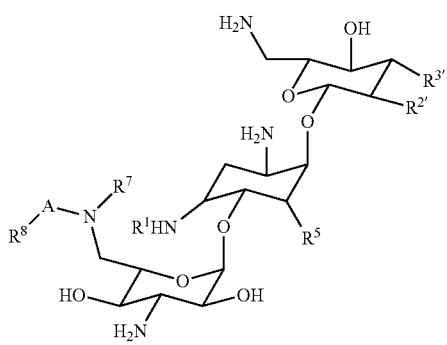

I

In some embodiments of the invention, $R^{2'}$ is —OH. In other embodiments, $R^{2'}$ is —NH$_2$.

In some embodiments of the invention, $R^{3'}$ is H. In other embodiments, $R^{3'}$ is —OH.

In some embodiments of the invention, $R^{2'}$ is —NH$_2$ and $R^{3'}$ is H.

In some embodiments of the invention, $R^1$ is H. In other embodiments, $R^1$ is —C(=NH)NH$_2$. In still other embodiments, $R^1$ is —C(=O)$R^{10}$.

In some embodiments of the invention, $R^{10}$ is (C$_1$-C$_{20}$) alkyl. In other embodiments of the invention, $R^{10}$ is (C$_3$-C$_{10}$) carbocycle. In some embodiments of the invention, $R^{10}$ is a (C$_3$-C$_9$)heterocycle. In some embodiments of the invention, $R^{10}$ is a —(C$_1$-C$_8$)alkyl(C$_3$-C$_{10}$)carbocycle. In still other embodiments of the invention, $R^{10}$ is a —(C$_1$-C$_8$)alkyl(C$_3$-C$_9$)heterocycle. In some embodiments of the invention, in the alkyl portion of $R^{10}$ [that is, when $R^{10}$ is (C$_1$-C$_{20}$)alkyl, (C$_1$-C$_8$)alkyl(C$_3$-C$_{10}$)carbocycle, or (C$_1$-C$_8$)alkyl(C$_3$-C$_9$)heterocycle], one or two —CH— may be replaced with —N—. In other embodiments of the invention in which $R^{10}$ contains an alkyl portion, two —CH— may be replaced by —C=C—. In still other embodiments in which $R^{10}$ contains an alkyl portion, one or two —CH$_2$— may be replaced by —O—, —S—, —SO—, —SO$_2$—, —C≡C—, a (C$_3$-C$_{10}$)carbocycle or a (C$_3$-C$_6$)heterocycle. In yet other embodiments of the invention, $R^{10}$ may be —(C$_1$-C$_{20}$)alkyl, —(C$_3$-C$_{10}$)carbocycle, —(C$_3$-C$_9$)heterocycle, —(C$_1$-C$_8$)alkyl(C$_3$-C$_{10}$)carbocycle, or —(C$_1$-C$_8$)alkyl(C$_3$-C$_9$)heterocycle additionally substituted with one, two or three substituents. In some embodiments, these substituents are chosen independently from —CH$_3$, —OH, —NH$_2$, —COOH, =O, —NHCONH$_2$, —NHC(=NH)NH$_2$, —CN or halogen.

In some embodiments of the invention, $R^1$ is —C(=O)$R^{10}$. In some of these embodiments, $R^{10}$ is (C$_1$-C$_{15}$)alkyl. In other embodiments of the invention, $R^{10}$ is (C$_3$-C$_6$)carbocycle. In some embodiments of the invention, $R^{10}$ is a (C$_3$-C$_5$)heterocycle. In some embodiments of the invention, $R^{10}$ is a —(C$_1$-C$_3$)alkyl(C$_3$-C$_6$)carbocycle. In still other embodiments of the invention, $R^{10}$ is a —(C$_1$-C$_3$)alkyl(C$_3$-C$_5$)heterocycle. As above, in some embodiments of the invention, in the alkyl portion of $R^{10}$ [that is, when $R^{10}$ is (C$_1$-C$_{15}$)alkyl, —(C$_1$-C$_3$)alkyl(C$_3$-C$_6$)carbocycle, or —(C$_1$-C$_3$)alkyl(C$_3$-C$_5$)heterocycle], one or two —CH— may be replaced with —N—. In other embodiments of the invention in which $R^{10}$ contains an alkyl portion, two —CH— may be replaced by —C=C—. In still other embodiments in which $R^{10}$ contains an alkyl portion, one or two —CH$_2$— may be replaced by —O—, —S—, —SO—, —SO$_2$—, —C≡C—, a (C$_3$-C$_{10}$)carbocycle or a (C$_3$-C$_6$)heterocycle. In yet other embodiments of the invention, $R^{10}$ may be —(C$_1$-C$_{15}$)alkyl, —(C$_3$-C$_6$)carbocycle, —(C$_3$-C$_5$)heterocycle, —(C$_1$-C$_3$)alkyl(C$_3$-C$_6$)carbocycle, or —(C$_1$-C$_3$)alkyl(C$_3$-C$_5$)heterocycle additionally substituted with one, two or three substituents. In some embodiments, these substituents are chosen independently from —CH$_3$, —OH, —NH$_2$, —COOH, =O, —NHCONH$_2$, —NHC(=NH)NH$_2$, —CN or halogen. In yet other embodiments of the invention, $R^{10}$ is selected from optionally substituted cyclopropyl, cyclobutyl, cyclopentyl, cyclohexyl, phenyl, pyrrole, imidazole, furan, tetrahydrofuran, piperidine, imidazolylmethyl and (C$_1$-C$_{10}$)alkyl. In other embodiments, $R^{10}$ is (C$_1$-C$_{10}$)alkyl in which one or two —CH— may be replaced with —N—. In still other embodiments, two —CH— may be replaced by —C=C—, and one or two —CH$_2$— may be replaced by —O—, —S—, —SO—, —SO$_2$— or —C≡C. In some embodiments, $R^{10}$ is the descarboxy residue of a natural α-amino acid. In other embodiments, $R^{10}$ is —CH($R^{11}$)—(CH$_2$)$_n$—NHR$^{12}$. In still other embodiments, $R^{10}$ is —(CH$_2$)$_n$—$R^{13}$. In some embodiments, —C(=O)$R^{10}$ is 4-amino-2-hydroxybutyryl.

In some embodiments, n is zero. In other embodiments, n is one. In other embodiments, n is two. In other embodiments, n is three. In other embodiments, n is four. In other embodiments, n is five. In other embodiments, n is six.

In some embodiments, $R^{11}$ is —OH. In other embodiments, $R^{11}$ is —NH$_2$.

In some embodiments, $R^{12}$ is H. In other embodiments, $R^{12}$ is (C$_1$-C$_6$)haloalkyl. In still other embodiments, $R^{12}$ is —C(=NH)NH$_2$. In yet other embodiments, $R^{12}$ is the deshydroxy residue of a natural α-amino acid.

In some embodiments, $R^{13}$ is —OH. In some embodiments, $R^{13}$ is optionally substituted phenyl. In some embodiments, $R^{13}$ is optionally substituted 5- or 6-membered ring heterocycle.

In some embodiments, $R^5$ is H. In some embodiments, $R^5$ is halogen. In other embodiments, $R^5$ is —$N_3$. In still other embodiments, $R^5$ is ($C_1$-$C_4$)alkynyl. In some embodiments, $R^5$ is —$NHR^{50}$. In some embodiments, $R^5$ is fluorine.

In some embodiments of the invention, $R^{50}$ is H. In some embodiments of the invention, $R^{50}$ is ($C_3$-$C_{10}$)carbocycle. In some embodiments of the invention, $R^{50}$ is ($C_3$-$C_9$)heterocycle. In some embodiments of the invention, $R^{50}$ is —($C_1$-$C_8$)alkyl($C_3$-$C_{10}$)carbocycle. In some embodiments of the invention, $R^{50}$ is —($C_1$-$C_8$)alkyl($C_3$-$C_9$)heterocycle. In some embodiments of the invention, $R^{50}$ is the deshydroxy residue of an aminoacid. In some embodiments, $R^{50}$ is selected from H, cyclopropyl, cyclopropylmethyl, pyrrolidinyl, and the deshydroxy residue of citrulline or serine.

In some embodiments of the invention, $R^7$ is H. In some embodiments of the invention, $R^7$ is ($C_1$-$C_6$)alkyl. In some embodiments of the invention, $R^7$ is hydroxy($C_1$-$C_6$)alkyl.

In some embodiments of the invention, $R^8$ is ($C_1$-$C_{20}$)alkyl. In some embodiments of the invention, $R^8$ is ($C_3$-$C_{10}$)carbocycle. In some embodiments of the invention, $R^8$ is ($C_3$-$C_9$)heterocycle. In some embodiments of the invention, $R^8$ is —($C_1$-$C_8$)alkyl($C_3$-$C_{10}$)carbocycle. In some embodiments of the invention, $R^8$ is —($C_1$-$C_8$)alkyl($C_3$-$C_9$)heterocycle. In some embodiments of the invention, $R^8$ is C(=NH)$NH_2$. In some embodiments of the invention, $R^8$ is $NR^{80}R^{81}$. In some embodiments of the invention, in the alkyl portion of $R^8$ [that is, when $R^8$ is ($C_1$-$C_{20}$)alkyl, —($C_1$-$C_8$)alkyl($C_3$-$C_{10}$)carbocycle, or —($C_1$-$C_8$)alkyl($C_3$-$C_9$)heterocycle], one or two —CH— may be replaced with —N—. In other embodiments of the invention in which $R^8$ contains an alkyl portion, two —CH— may be replaced by —C=C—. In still other embodiments in which $R^8$ contains an alkyl portion, one or two —$CH_2$— may be replaced by —O—, —S—, —SO—, —$SO_2$—, —C≡C—, a ($C_3$-$C_{10}$)carbocycle or a ($C_3$-$C_6$)heterocycle. In yet other embodiments of the invention, $R^8$ may be ($C_1$-$C_{20}$)alkyl, ($C_3$-$C_{10}$)carbocycle, ($C_3$-$C_9$)heterocycle, —($C_1$-$C_8$)alkyl($C_3$-$C_{10}$)carbocycle, or —($C_1$-$C_8$)alkyl($C_3$-$C_9$)heterocycle additionally substituted with one, two or three substituents. In some embodiments, these substituents are chosen independently from —$CH_3$, —$CH_2CH_3$, —OH, —$CH_2OH$, —$NH_2$, —$CH_2NH_2$, —COOH, =O, —NHCON$H_2$, —NHC(=NH)$NH_2$, —CN or halogen.

In some embodiments of the invention, $R^{80}$ is H. In other embodiments of the invention, $R^{80}$ is ($C_1$-$C_6$)alkyl.

In some embodiments of the invention, $R^{81}$ is H. In other embodiments of the invention, $R^{81}$ is ($C_1$-$C_6$)alkyl.

In some embodiments of the invention, A is a direct bond. In some embodiments of the invention, A is —(C=O)—. In other embodiments of the invention, A is —C(=O)O—. In still other embodiments of the invention, A is —NH(C=O)—. In yet other embodiments of the invention, A is —(C=O)NH—. In some embodiments of the invention, A is —NH(C=O)NH—. In some embodiments of the invention, A is —(C=S)NH—. In other embodiments of the invention, A is —NH(C=S)—. In some embodiments of the invention, A is —NH(C=S)NH—.

In some embodiments of the invention, $R^7$ and $R^8$A, taken together with the nitrogen to which they are attached, form a ($C_3$-$C_9$)heterocycle. In some of these embodiments, the ($C_3$-$C_9$)heterocycle is optionally substituted with one, two or three substituents chosen independently from —$CH_3$, —$CH_2CH_3$, —OH, —$CH_2OH$, —$NH_2$, —$CH_2NH_2$, —COOH, =O, —NHCON$H_2$, —NHC(=NH)$NH_2$, —CN and halogen.

In some embodiments, $R^7$ and $R^8$A, taken together with the nitrogen to which they are attached, form a ($C_3$-$C_6$)heterocycle. In some embodiments, this ($C_3$-$C_6$)heterocycle may be optionally substituted with from one to three substituents chosen independently from —$CH_3$, —$CH_2CH_3$, —OH, —$CH_2OH$, —$NH_2$, —$CH_2NH_2$, —COOH, =O, —NHCON$H_2$, —NHC(=NH)$NH_2$, —CN and halogen. In other embodiments, $R^7$ and $R^8$A, taken together with the nitrogen to which they are attached, form a piperidine, piperazine, tetrahydropyrimidine or pyrrolidine, any of which are optionally substituted with —$CH_3$, —$CH_2CH_3$, —OH, —$CH_2OH$, —$NH_2$, —$CH_2NH_2$, —COOH, =O, —NHCON$H_2$, —NHC(=NH)$NH_2$, —CN or halogen.

In some embodiments, A is a direct bond and $R^7$ and $R^8$ are chosen independently from ($C_1$-$C_6$)alkyl and hydroxy($C_1$-$C_6$)alkyl.

In some embodiments of the invention, $R^7$ is H; A is chosen from a direct bond, —(C=O)—, —C(=O)O—, and —NH(C=O)—; and $R^8$ is chosen from ($C_1$-$C_{15}$)alkyl, ($C_3$-$C_{10}$)carbocycle, ($C_3$-$C_6$)heterocycle, —($C_1$-$C_3$)alkyl($C_3$-$C_6$)carbocycle, —($C_1$-$C_3$)alkyl($C_3$-$C_6$)heterocycle, —N($CH_3$)$_2$— $NH_2$, and —C(=NH)$NH_2$. In some of these embodiments, one or two of the —CH— residues of the ($C_1$-$C_{15}$)alkyl or the ($C_1$-$C_3$)alkyl portion of the —($C_1$-$C_3$)alkyl($C_3$-$C_6$)carbocycle or —($C_1$-$C_3$)alkyl($C_3$-$C_6$)heterocycle may be may be replaced with —N—, two —CH— may be replaced by —C=C—, or one or two —$CH_2$— may be replaced by —O—, —$SO_2$—, —C≡C—, a ($C_5$-$C_6$)carbocycle or a ($C_3$-$C_4$)heterocycle. Additionally or alternatively, in some of these embodiments, the ($C_1$-$C_{15}$)alkyl, ($C_3$-$C_{10}$)carbocycle, ($C_3$-$C_6$)heterocycle, —($C_1$-$C_3$)alkyl($C_3$-$C_6$)carbocycle, or —($C_1$-$C_3$)alkyl($C_3$-$C_6$)heterocycle may be additionally substituted with from one to three substituents chosen independently from —$CH_3$, —$CH_2CH_3$, —OH, —$CH_2OH$, —$NH_2$, —COOH, =O, —NHCON$H_2$, —NHC(=NH)$NH_2$, and halogen.

In some embodiments, $R^7$ is H; A is a direct bond; and $R^8$ is chosen from —N($CH_3$)$_2$, —$NH_2$, and —C(=NH)$NH_2$.

In some embodiments of the invention, $R^7$ is H; A is chosen from a direct bond and —(C=O)—; and $R^8$ is chosen from ($C_1$-$C_{15}$)alkyl, ($C_3$-$C_{10}$)carbocycle, ($C_3$-$C_6$)heterocycle, —($C_1$-$C_3$)alkyl($C_3$-$C_6$)carbocycle, and —($C_1$-$C_3$)alkyl($C_3$-$C_6$)heterocycle. In some of these embodiments, the ($C_1$-$C_{15}$) alkyl, ($C_3$-$C_{10}$)carbocycle, ($C_3$-$C_6$)heterocycle, —($C_1$-$C_3$)alkyl($C_3$-$C_6$)carbocycle, or —($C_1$-$C_3$)alkyl($C_3$-$C_6$)heterocycle may be additionally substituted with from one to three substituents chosen independently from —$CH_3$, —$CH_2CH_3$, —OH, —$CH_2OH$, —$NH_2$, —COOH, =O, —NHCON$H_2$, —NHC(=NH)$NH_2$, and halogen.

In some embodiments of the invention, $R^7$ is H; A is chosen from a direct bond, —(C=O)—, —C(=O)O—, and —NH(C=O)—; and $R^8$ is ($C_1$-$C_{15}$)alkyl. In some of these embodiments, one or two —CH— of the ($C_1$-$C_{15}$)alkyl may be replaced with —N—, two —CH— may be replaced by —C=C—, or one or two —$CH_2$— may be replaced by —O—, —$SO_2$—, —C≡C—, cyclopentyl, cyclohexyl, furan or dioxole. In still other embodiments, the ($C_1$-$C_{15}$)alkyl or replaced ($C_1$-$C_{15}$)alkyl may additionally be substituted with from one to three substituents chosen independently from —$CH_3$, —$CH_2CH_3$, —OH, —$CH_2OH$, —$NH_2$, —COOH, =O, —NHCON$H_2$, —NHC(=NH)$NH_2$, and halogen.

In some embodiments of the invention, $R^7$ is H; A is a direct bond; and $R^8$ is ($C_1$-$C_6$)alkyl additionally substituted with one to or two substituents chosen independently from —OH, —NH$_2$, and —NHC(=NH)NH$_2$. In some of these embodiments, R$^8$ is aminopropyl. In some of these embodiments, R$^5$ is fluorine. In some of these embodiments, —(C=O)R$^{10}$ is 4-amino-2-hydroxybutyryl.

In some embodiments of the invention, R$^{10}$ is selected from optionally substituted cyclopropyl, cyclobutyl, cyclopentyl, cyclohexyl, phenyl, pyrrole, imidazole, furan, tetrahydrofuran, piperidine, imidazolylmethyl, (C$_1$-C$_{10}$)alkyl [in which one or two —CH— may be replaced with —N—, two —CH— may be replaced by —C=C—, and one or two —CH$_2$— may be replaced by —O—, —S—, —SO—, —SO$_2$— or —C≡C], the descarboxy residue of a natural α-amino acid, —CH(R$^{11}$)—(CH$_2$)$_n$—NHR$^{12}$, and —(CH$_2$)$_n$—R$^{13}$. In these embodiments, A is chosen from a direct bond and —(C=O)—, and R$^8$ is chosen from (C$_1$-C$_{15}$)alkyl, (C$_3$-C$_{10}$)carbocycle, (C$_3$-C$_6$)heterocycle, —(C$_1$-C$_3$)alkyl(C$_3$-C$_6$)carbocycle, and —(C$_1$-C$_3$)alkyl(C$_3$-C$_6$)heterocycle. The (C$_1$-C$_{15}$)alkyl, (C$_3$-C$_{10}$)carbocycle, (C$_3$-C$_6$)heterocycle, (C$_1$-C$_3$)alkyl(C$_3$-C$_6$)carbocycle, (C$_1$-C$_3$)alkyl(C$_3$-C$_6$)heterocycle may be additionally substituted with from one to three substituents chosen independently from —CH$_3$, —CH$_2$CH$_3$, —OH, —CH$_2$OH, —NH$_2$, —COOH, =O, —NHCONH$_2$, —NHC(=NH)NH$_2$, and halogen. In some of these embodiments, R$^5$ is chosen from H, fluorine, N$_3$ and —NHR$^{50}$, and R$^{50}$ is chosen from H, cyclopropyl, cyclopropylmethyl, pyrrolidinyl, and the deshydroxy residue of citrulline or serine.

In some embodiments, R$^{2'}$ is —NH$_2$ and R$^{3'}$ is H.

Throughout this specification the terms and substituents retain their definitions.

Alkyl is intended to include linear and branched hydrocarbon structures. A combination of alkyl with cycloalkyl such as —(C$_1$-C$_8$)alkyl(C$_3$-C$_{10}$)carbocycle would be, for example, cyclopropylmethyl. Lower alkyl refers to alkyl groups of from 1 to 6 carbon atoms. Examples of lower alkyl groups include methyl, ethyl, propyl, isopropyl, n-butyl, s-butyl and t-butyl, and the like. Preferred alkyl groups are those of C$_{20}$ or below. Cycloalkyl or carbocycle includes cyclic hydrocarbon groups of from 3 to 8 carbon atoms. Examples of cycloalkyl groups include c-propyl, c-butyl, c-pentyl, norbornyl and the like. Alkylene is a divalent alkyl residue, for example propylene is —CH$_2$CH$_2$CH$_2$—.

Alkoxy or alkoxyl refers to groups of from 1 to 6 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Similarly, alkylthio refers to groups of from 1 to 6 carbon atoms of a straight, branched, or cyclic configuration and combinations thereof attached to the parent structure through sulfur.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl as a substituent means an aryl ring attached to the parent structure via an alkyl residue. Examples are benzyl, phenethyl and the like. Heteroarylalkyl means a heteroaryl ring attached to the parent structure via an alkyl residue. Examples include, e.g., pyridinylmethyl, pyrimidinylethyl and the like.

Hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, camphoryl and naphthylethyl.

Unless otherwise specified, the term "carbocycle" is intended to include ring systems in which the ring atoms are all carbon but of any oxidation state. Thus (C$_3$-C$_{10}$) carbocycle refers to both non-aromatic and aromatic systems, including such systems as cyclopropane, benzene and cyclohexene. Carbocycle, if not otherwise limited, refers to monocycles, bicycles and polycycles.

Heterocycle means a cycloalkyl or aryl residue in which one to four of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

The term "halogen" means fluorine, chlorine, bromine or iodine. In one embodiment, halogen may be fluorine or chlorine.

As used herein, the term "optionally substituted" may be used interchangeably with "unsubstituted or substituted". The term "substituted" refers to the replacement of one or more hydrogen atoms in a specified group with a specified radical. In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

Virtually all of the compounds described herein contain one or more asymmetric centers and thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Substituents R$^n$ are generally defined when introduced and retain that definition throughout the specification and in all independent claims.

The term "residue of an amino acid" as used herein refers to an amino acid (as defined below) minus one hydroxyl or carboxyl that is considered part of the linkage to the parent aminoglycoside scaffold. When the "residue of the amino acid" is "deshydroxy", it will be minus the hydroxyl of the acid function. If the amino acid has two carboxyls (e.g. glutamic acid) the hydroxy can be from either carboxylic acid. When the "residue of the amino acid" is "descarboxy", it will be minus —COOH; if the amino acid has two carboxyls, either carboxylic acid can be removed. For example, in the molecule illustrated below:

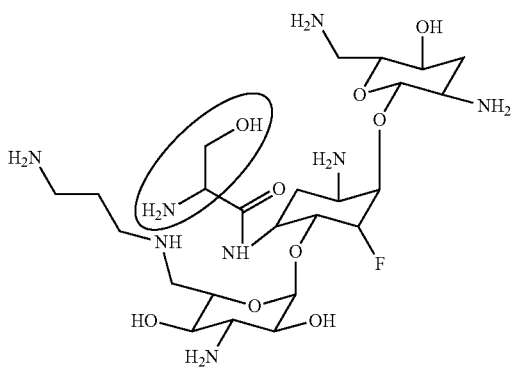

the circled residue $R^{10}$ is the descarboxy residue of the natural amino acid serine. Similarly in the molecule:

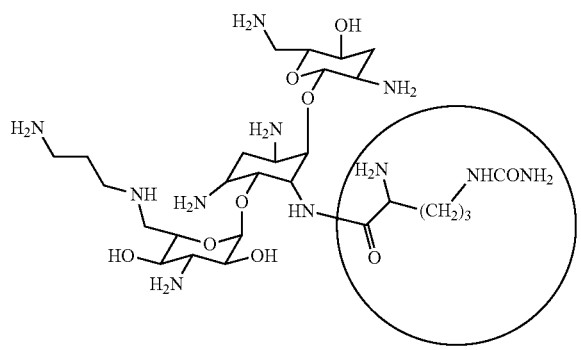

the circled residue $R^{50}$ is the deshydroxy residue of the natural amino acid citrulline. These and similar structures of amino acids that lack a functional group at the point of attachment to the glycoside scaffold are referred to herein as "residues of amino acids". One might also refer to them as amino acid fragments.

The term "amino acid" as used herein refers to the racemates and all optical isomers of the following naturally occurring α-amino acids: alanine, asparagine, aspartic acid, arginine, citrulline, cysteine, glutamic acid, glutamine, glycine, histidine, isoleucine, leucine, lysine, methionine, phenylalanine, proline, serine, threonine, tryptophan, tyrosine, valine, sarcosine, norvaline, norleucine, homoserine, allothreonine, hydroxynorvaline, statine, hydroxyproline, ornithine, 2-aminoadipic acid, penicillamine, homocysteine, S-methylcysteine, ethionine and phenylglycine. For the purpose of this invention, the term "amino acid" also includes a single naturally occurring β-amino acid, β-alanine.

As used herein, and as would be understood by the person of skill in the art, the recitation of "a compound"—unless expressly further limited—is intended to include salts of that compound. Thus, for example, the recitation "a compound of formula I" as depicted above, in which $R^1$ is —C(=NH)NH$_2$, would include salts in which $R^1$ is —C(=NH)NH$_3^+$X$^-$, wherein X is any counterion. In a particular embodiment, the term "compound of formula I" refers to the compound or a pharmaceutically acceptable salt thereof.

The compounds of the invention may be present as salts, i.e. cationic species. The term "pharmaceutically acceptable salt" refers to salts whose counter ion (anion) derives from pharmaceutically acceptable non-toxic acids including inorganic acids and organic acids. Suitable pharmaceutically acceptable anions for the compounds of the present invention include acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. Although pharmaceutically acceptable counter ions will be preferred for preparing pharmaceutical formulations, other anions are quite acceptable as synthetic intermediates. That is, pharmaceutically undesirable anions, such as iodide, oxalate, trifluoromethanesulfonate and the like, may be present when such salts are chemical intermediates.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2$H, $^3$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Among the isotopically altered compounds of the invention, deuterated, i.e. $^2$H, compounds are of particular interest. Selective incorporation of deuterium in place of hydrogen (deuteration) has the unique effect of retaining the biochemical potency and selectivity of physiologically active compounds while, in certain instances, modifying metabolic fate to substantially alter their overall therapeutic profile. In favourable cases, this modification has the potential to have a positive impact effect on safety, efficacy and/or tolerability. [See "The Development of Deuterium-Containing Drugs" by Roger Tung, *Innovations in Pharmaceutical Technology* March 2010 and U.S. Pat. Nos. 7,514,068; 7,608,737; 7,678,914 and others.] Tritiated, i.e. $^3$H, and carbon-14, i.e., $^{14}$C, radioisotopes are in certain circumstances preferred for their ease in preparation and detectability. Compounds that contain isotopes $^{11}$C, $^{13}$N, $^{15}$O and $^{18}$F are well suited for positron emission tomography. Radiolabeled compounds described above can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

A comprehensive list of abbreviations utilized by organic chemists appears in the first issue of each volume of the Journal of Organic Chemistry. The list, which is typically presented in a table entitled "Standard List of Abbreviations", is incorporated herein by reference. The following abbreviations and terms have the indicated meanings throughout:
Ac=acetyl
Boc=t-butyloxy carbonyl
Bredereck's Reagent=tert-butoxy-bis-(dimethylamino) methane
Bu=butyl
c-=cyclo
DCC=dicyclohexyl carbodiimide
DIPEA=diisopropylethylamine
DMAP=dimethylaminopyridine
DMF=N,N-dimethylformamide
EDC=1-(3-(dimethylamino)propyl)-3-ethyl-carbodiimide hydrochloride
EtOAc=ethyl acetate
HOBt=hydroxybenzotriazole
HOSU=N-hydroxysuccinimide
LiHMDS=lithium hexamethyldisilazide
MCPBA=meta-Chloroperoxybenzoic Acid
Me=methyl
MIC=minimum inhibitory concentration
MMP=matrix metalloproteinase
NaH=sodium hydride
NHS=N-hydroxysuccinimide
Ph=phenyl
PhOH=phenol
rt=room temperature
sat'd=saturated
TBDMS=t-butyldimethylsilyl
TFA=trifluoroacetic acid
THF=tetrahydrofuran
TIPS=triisopropylsilyl
TMS=trimethylsilyl The following abbreviations are also used in the description of the substituents in the text of this application:

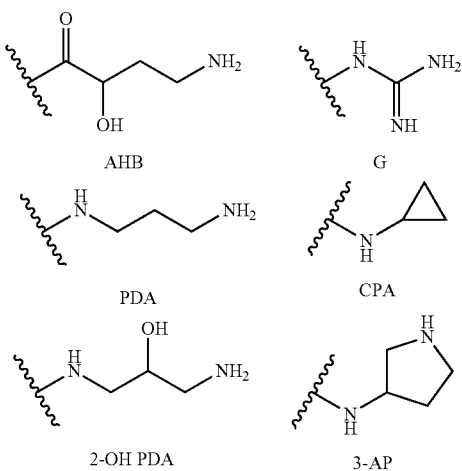

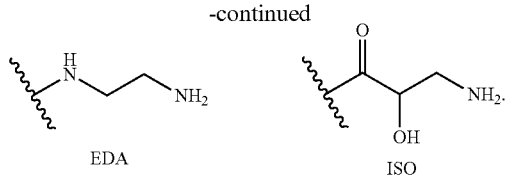

It may happen that residues in the substrate of interest require protection and deprotection during the synthesis procedure. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. Parenteral pharmaceutical compositions, oral dosage forms and topical pharmaceutical compositions are preferred. Tablets, capsules, intraocular topical formulations and parenteral solutions are common among aminoglycosides. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a waterin-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

Table 1 (below) presents representative members of the genus of the invention:

| Example # | ID Code | R1 | R5 | R2' | R3' | R8—A—N(R7)— |
|---|---|---|---|---|---|---|
| 1 | SXP1212-56"-7 | [structure] | F | OH | OH | [structure] |
| 2 | SXP1212-56"-8 | [structure] | F | OH | OH | [structure] |
| 3 | SXP1212-56"-9 | [structure] | F | OH | OH | [structure] |
| 4 | SXP1212-56"-10 | [structure] | F | OH | OH | [structure] |
| 5 | SXP1212-56"-16 | [structure] | F | OH | OH | [structure] |
| 6 | SXP1212-56"-17 | [structure] | F | OH | OH | [structure] |

-continued

| Example # | ID Code | R1 | R5 | R2' | R3' | R8—A—N(R7)— |
|---|---|---|---|---|---|---|
| 7 | SXP1212-56"-21 | (3S)-3-hydroxy-5-amino-pentanoyl | N₃ | OH | OH | L-citrulline amide |
| 8 | SXP1212-56"-25 | (3S)-3-hydroxy-5-amino-pentanoyl | NH₂ | OH | OH | L-citrulline amide |
| 9 | SXP1212-56"-27 | (3S)-3-hydroxy-5-amino-pentanoyl | NH₂ | OH | OH | cyclopropyl-NH- |
| 10 | SXP1212-56"-28 | (3S)-3-hydroxy-5-amino-pentanoyl | F | OH | OH | cyclopropanecarbonyl hydrazide |
| 11 | SXP1212-56"-29 | (3S)-3-hydroxy-5-amino-pentanoyl | F | OH | OH | 2-morpholinoethylamino |
| 12 | SXP1212-56"-30 | (3S)-3-hydroxy-5-amino-pentanoyl | F | OH | OH | (2-morpholinoethyl)thiosemicarbazide |
| 13 | SXP1212-56"-31 | (3S)-3-hydroxy-5-amino-pentanoyl | F | OH | OH | 3-(2-oxopyrrolidin-1-yl)propylamino |
| 14 | SXP1212-56"-32 | (3S)-3-hydroxy-5-amino-pentanoyl | F | OH | OH | 2-(piperidin-4-yl)ethylamino |
| 15 | SXP1212-56"-33 | (3S)-3-hydroxy-5-amino-pentanoyl | F | OH | OH | hexadecan-2-ylamino |
| 16 | SXP1212-56"-34 | (3S)-3-hydroxy-5-amino-pentanoyl | F | OH | OH | (5-methylhexan-2-yl)amino |

-continued

| Example # | ID Code | Substituents | | | | |
|---|---|---|---|---|---|---|
| | | R1 | R5 | R2' | R3' | R8—A—N(R7)— |
| 17 | SXP1212-56''-35 | [3-amino-1-hydroxypropanoyl group, (S)-OH] | F | OH | OH | heptan-2-ylamino |
| 18 | SXP1212-56''-36 | [3-amino-1-hydroxypropanoyl group] | F | OH | OH | cyclobutylamino |
| 19 | SXP1212-56''-37 | [3-amino-1-hydroxypropanoyl group] | F | OH | OH | cyclopentylamino |
| 20 | SXP1212-56''-38 | [3-amino-1-hydroxypropanoyl group] | F | OH | OH | cyclohexylamino |
| 21 | SXP1212-56''-39 | [3-amino-1-hydroxypropanoyl group] | F | OH | OH | piperidin-4-ylamino |
| 22 | SXP1212-56''-40 | [3-amino-1-hydroxypropanoyl group] | F | OH | OH | pyrrolidin-3-ylamino |
| 23 | SXP1212-56''-41 | [3-amino-1-hydroxypropanoyl group] | F | OH | OH | (3-aminoazetidin-1-yl... via NH) |
| 24 | SXP1212-56''-42 | [3-amino-1-hydroxypropanoyl group] | F | OH | OH | (3-aminopropyl)amino |
| 25 | SXP1212-56''-43 | [3-amino-1-hydroxypropanoyl group] | F | OH | OH | (cyanomethyl)amino |
| 26 | 2554 | [3-amino-1-hydroxypropanoyl group] | F | NH$_2$ | H | azetidin-3-ylamino |

-continued

| Example # | ID Code | R1 | R5 | R2' | R3' | R8—A—N(R7)— |
|---|---|---|---|---|---|---|
| 27 | 2523 | (structure: C(=O)-CH(OH)-CH2-CH2-NH2) | F | NH2 | H | (structure: -N(H)-CH2CH2CH2-NH2) |
| 28 | 2524 | (structure: C(=O)-CH(OH)-CH2-CH2-NH2) | F | NH2 | H | (structure: -N(H)-CH2-CH(OH)-CH2-NH2) |
| 29 | 2525 | (structure: C(=O)-CH(OH)-CH2-CH2-NH2) | F | NH2 | H | (structure: -N(H)-CH2-azetidinyl-NH) |

For evaluation of efficacy, we assembled panels of representative gram-negative pathogens, including *Pseudomonas aeruginosa* (Pae, PAWT, ATCC #27853), *Klebsiella pneumoniae* (Kpn, KPWT, ATCC #700603), *Acinetobacter baumannii* (Aba, ABWT, ATCC #BAA-747) and *Escherichia coli* (Eco, ECWT, ATCC #25922). These reference strains are useful indicator organisms to characterize compound activity against bacteria from a pathogenic genus in the absence of multiple resistance mechanisms. Two strains (PAWT and ECWT) are reference strains cited within the Clinical and Laboratory Standards Institute (CLSI) Standards for susceptibility testing by Minimum Inhibitory Concentration (MIC) (SXPS2) and are well suited for quality control. ABWT and ECWT are widely susceptible to aminoglycoside antibiotics, whereas PAWT and KPWT harbor a single aminoglycoside-modifying enzyme (AGME) that targets 4,6-substituted-2-deoxystreptamine AGs.

TABLE 2

MIC values of reference AGs against indicator strains.

| | MIC (µg/mL) | | | |
|---|---|---|---|---|
| Standard AG | PAWT | KPWT | ABWT | ECWT |
| tobramycin | 0.25 | 8 | 0.25 | 1 |
| sisomycin | 0.25-0.5 | 1-2 | 0.125-0.25 | 0.25-0.5 |
| dibekacin | 0.25-0.5 | 16 | 0.25 | 1-2 |
| arbekacin | 0.5 | 0.25-0.5 | 0.5 | 1 |
| gentamycin | 1 | 8 | 0.25-0.5 | 0.5 |
| amikacin | 1-2 | 1 | 1 | 2-4 |
| streptomycin | 16 | 1-2 | 2-4 | 4 |
| kanamycin B | 16 | 16 | 0.5-1 | 2 |
| neomycin | 32 | 4-8 | 0.25-0.5 | 1 |
| kanamycin A | >64 | 32 | 1 | 4 |
| spectinomycin | >64 | 64 | 16 | 8-16 |

*Pseudomonas aeruginosa* is a prominent nosocomial pathogen. In addition to intrinsic antibiotic resistance to several antibiotics, *Pseudomonas* has acquired multiple additional mechanisms of resistance. As a result, therapeutic options for the treatment of infections caused by *Pseudomonas aeruginosa* are limited. We acquired clinical isolates of *Pseudomonas aeruginosa* (Micromyx LLC, Kalamazoo, Mich.), and used this panel to test compounds for Pseudomonicidal activity. The panel includes PAWT, two clinical isolates with intermediate aminoglycoside resistance (PR1 and PR2), and a third clinical isolate (PR3) possessing high-level, efflux-mediated, pan-aminoglycoside resistance ("impermeable"). For each strain and antibiotic, the mechanism(s) of resistance was inferred from the resistance profile. The presence of specific AGMEs was confirmed by colony PCR.

TABLE 3

Potency of reference and test compounds against *Pseudomonas aeruginosa* wild type and resistant strains:

| | MIC (µg/mL) | | | |
|---|---|---|---|---|
| | PAWT | PR1 | PR2 | PR3 |
| TOB | 0.25 | 2 | >64 | >64 |
| DIB | 0.25-0.5 | 4 | >64 | >64 |
| SISO | 0.25-0.5 | 4 | >64 | >64 |
| ARB | 0.5 | 8 | 8-16 | 16 |
| GEN | 1 | 8 | >64 | >64 |
| AMK | 1-2 | 8 | 8-16 | 64 |
| STREP | 16 | 64 | 16 | 64 |
| KAN-B | 16 | 64 | >64 | >64 |
| NEO | 32 | 32 | 8-16 | >64 |
| KAN-A | >64 | >64 | >64 | >64 |
| SPE | >64 | >64 | >64 | >64 |
| SXP1212-56''-7 | 4 | 16 | 16 | 128 |
| SXP1212-56''-8 | 4 | 8 | 8 | 64 |
| SXP1212-56''-16 | 1 | 2-8 | <0.25-4 | 32 |
| 2523 | 0.25 | 1-2 | 0.5 | 4 |
| 2554 | 0.25 | 2 | 0.5 | 8 |
| 2524 | 0.25 | 4 | 0.5 | 8 |
| 2525 | 0.25-0.5 | 8 | 1 | 8 |

Next, we considered whether the SAR observed against select Pae strains 1, 2 or 3 was indicative of general potency against *Pseudomonas aeruginosa*. To assess this, a panel of more than fifty resistant contemporary clinical isolates of *Pseudomonas aeruginosa* were obtained from multiple sources including JMI Laboratories (North Liberty, Iowa), Pfizer (Groton, Conn.), Micromyx (Kalamazoo, Mich.), Dr. J. Chow (Wayne State University). Strains were characterized for resistance to a wide variety of classes of antibiotics including aminoglycosides, β-lactams and fluoroquinolones. The MIC$_{90}$ values for fifteen antibiotics (amikacin, gentamycin, tobramycin, ceftazidime, cefepime, piperacillin, piperacillin/tazobactam, aztreonam, ceftriaxone, imipenem, meropenem, doripenem, ertapenem, ciprofloxacin and levofloxacin) against these fifty resistant contemporary clinical isolates of *Pseudomonas aeruginosa* were ≥64 μg/mL. This reflects the difficulty in treating clinical *Pseudomonas aeruginosa* infections. Aminoglycoside and β-lactam profiling showed the presence of most all representative aminoglycoside modifying enzymes, efflux and β-lactamase mechanisms of resistance. Using this stringent panel, we tested a subset of compounds of the invention (Table 4).

TABLE 4

| | MIC (μg/mL) | | | | |
|---|---|---|---|---|---|
| | *Pseudomonas aeruginosa* | | | | |
| SXP # | PAWT | PR1 | PR2 | PR3 | MIC$_{90}$ |
| SXP1212-56"-7 | 4 | 16 | 16 | 128 | |
| SXP1212-56"-8 | 4 | 8 | 8 | 64 | |
| SXP1212-56"-16 | 1 | 2-8 | <0.25-4 | 32 | |
| 2523 | 0.25 | 1-2 | 0.5 | 4 | 4 |
| 2524 | 0.25 | 4 | 0.5 | 8 | 4 |
| 2554 | 0.25 | 2 | 0.5 | 8 | 4 |
| 2525 | 0.25-0.5 | 8 | 1 | 8 | 4 |

In general, MIC$_{90}$ values were within a single dilution of MIC values against PR3, suggesting that PR3 is an appropriate indicator strain.

*Klebsiella pneumoniae* (Kpn) and *Escherichia coli* (Eco) are gram-negative (like Pae), enteric pathogens with increasing clinical relevance. Many clinical isolates of Kpn and Eco harbor extended-spectrum beta-lactamases and are no longer sensitive to most beta-lactam antibiotics. We acquired clinical isolates of *Klebsiella pneumoniae* and *Escherichia coli* (Micromyx LLC, Kalamazoo, Mich.) and used this panel to test compounds for anti-enteric activity. The aminoglycoside resistance profile of clinical Eco isolates is similar to the aminoglycoside resistance profile of Kpn isolates. Indeed, MIC comparison of Eco and Kpn strains are similar (data not shown). As a result, we focused on Kpn and assembled a screening panel that included *Klebsiella pneumoniae* wild type (KPWT), two clinical isolates with intermediate aminoglycoside resistance (KR1 and KR2), and a third clinical isolate (KR3) possessing high-level aminoglycoside resistance. No single reference AG (amikacin, gentamycin, tobramycin, streptomycin, sisomycin, neomycin, arbekacin, dibekacin, kanamycin B, spectinomycin or kanamycin A) demonstrated acceptable potency against all strains tested. KAN A, KAN B, and DIB showed limited to no activity against the test panel and only ARB and AMK showed potency against 3 of 4 strains tested. Strain KR3 was largely recalcitrant to aminoglycoside exposure (except GEN). Recognizing strain KR3 is largely recalcitrant to AGs, we tested compounds of the invention against this panel and noted potency against KR3 (followed by KR2 and KR1).

As in the case of *Pseudomonas aeruginosa*, we considered whether the SAR observed against select *Klebsiella pneumoniae* strains 1, 2 or 3 was indicative of general potency. The MIC$_{90}$ values for fifteen antibiotics (amikacin, gentamycin, tobramycin, ceftazidime, cefepime, piperacillin, piperacillin/tazobactam, aztreonam, ceftriaxone, imipenem, meropenem, doripenem, ertapenem, ciprofloxacin and levofloxacin) against fifty resistant contemporary clinical isolates of *Klebsiella pneumoniae* were once again ≥64 μg/mL. Using this stringent *Klebsiella pneumoniae* panel, we tested a subset of compounds of the invention. The results, as well as MIC$_{90}$ results against a panel of *E. coli* strains, are shown in Table 5:

TABLE 5

| MIC values against Enterobacteriaceae | | | | | | |
|---|---|---|---|---|---|---|
| | *Klebsiella pneumonia* | | | | | *E. coli* |
| SXP # | KPWT | KR1 | KR2 | KR3 | MIC$_{90}$ | MIC$_{90}$ |
| SXP1212-56"-16 | <0.25 | 0.5-1 | 1 | 16 | | |
| 2554 | 0.125 | 0.25 | 0.125 | 0.25-0.5 | 0.5 | 2 |
| 2524 | 0.5 | 0.5-1 | 0.5 | 0.5-1 | 1 | 2-4 |
| 2525 | 0.5 | 1 | 0.5 | 1 | 1 | 2 |
| 2523 | 0.5-1 | 0.5-1 | 0.5-1 | 1 | 1 | 2 |

*Acinetobacter baumannii* is another clinically important and very challenging gram negative pathogen. Members of the *Acinetobacter* genus, including *baumannii*, have a remarkable ability to upregulate and acquire resistance determinants. Coupled with its ability to survive for prolonged periods in a hospital environment, *A. baumannii* is an emerging threat for healthcare institutions globally. We acquired clinical isolates of *Acinetobacter baumannii* and used this panel to test compounds for anti-Acinetobacter activity. We first tested reference AGs against our panel of Aba strains. As expected, clinical Aba isolates were significantly more resistant to reference AGs than *Acinetobacter baumannii* wild type (ABWT). Of the 4,6-disubstituted-2-deoxystreptamine reference compounds, only arbekacin demonstrated activity (≤8 μg/mL) against 3 of the 4 indicator strains.

As in the case of *Pseudomonas aeruginosa* and *Klebsiella pneumoniae*, we considered whether the SAR observed against select *Acinetobacter baumannii* strains 1, 2 or 3 was indicative of general potency. The MIC$_{90}$ values for the fifteen antibiotics against fifty resistant contemporary clinical isolates of *Acinetobacter baumannii* were ≥32 μg/mL. Using this stringent *Acinetobacter baumannii* panel, we tested a subset of compounds of the invention. The results are shown in Table 6:

TABLE 6

| MIC values against *Acinetobacter baumannii* | | | | | |
|---|---|---|---|---|---|
| | MIC (μg/mL) | | | | |
| | *Acinetobacter baumannii* | | | | |
| SXP # | ABWT | AB1 | AB2 | AB3 | MIC$_{90}$ |
| 2554 | 0.25 | 0.5 | 0.25-0.5 | 2-4 | 2 |
| 2524 | 0.5 | 2 | 1 | 8 | 2 |
| 2525 | 0.5 | 2-4 | 1 | 8 | 2 |
| 2523 | 0.5 | 2-4 | 1 | 4-8 | 4 |

The compound identified as SXP 2523 was selected for further testing in vivo. Twenty male Sprague Dawley rats were pre-treated with cyclophosphamide to render them neutropenic on day −4 and day −1 with 100 mg/kg and 75 mg/kg respectively. Rats were infected with *P. aeruginosa* 6294 MLP-3, via injection into the right thigh muscle of 0.1 mL per rat. Two hours post infection rats were treated intravenously with either SXP-2523 or amikacin in a total dose of 10 or 60 mg/kg, respectively. The test article and control agent were delivered at 2, 4, and 6 hours post infection. Five rats were treated with each drug concentration. One group of five rats was euthanized at initiation of treatment and thigh CFUs were processed (T=Rx). Twenty-four hours post infection rats were euthanized by $CO_2$ inhalation. The right thigh muscles of the rats were aseptically removed, weighed, homogenized, serially diluted, and plated on MacConkey medium. The plates were incubated overnight at 37° C. in 5% $CO_2$. CFU per gram of thigh was calculated by enumerating the plated colonies then adjusting for serial dilutions and the weight of the thigh. The following table 7 summarizes the results Table 6:

TABLE 7

Rat neutropenic thigh model results

| test article | Total Drug Concentration (mg/kg) | n | Log CFU/ thigh | St. Dev. | Change from 24 hr. control | Change from T = Rx controls |
|---|---|---|---|---|---|---|
| T = Rx | — | 5 | 4.18 | 0.25 | | |
| 24 hr controls | — | 5 | 7.26 | 0.37 | | 3.08 |
| SXP-2523 | 10.0 | 5 | 6.55 | 0.44 | −0.71 | 2.37 |
| Amikacin | 60.0 | 5 | 5.77 | 0.37 | −1.49 | 1.59 |

It can be seen that SXP-2523 is effective against *P. aeruginosa* in an appropriate animal model. The relative potency vis-à-vis amikacin cannot be determined from this experiment because the dose of SXP-2523 was one-sixth the dose of amikacin.

The compound identified as SXP 2523 was further tested in vivo against a resistant strain of *P. aeruginosa*. Twenty male Sprague Dawley rats were rendered neutropenic by treatment with cyclophosphamide on day −4 and day −1 with 100 mg/kg and 75 mg/kg, respectively. Rats were infected with *P. aeruginosa* 6294 MLP-3, via injection into the right thigh muscle of 0.1 mL per rat. Two hours post infection rats were treated intravenously with either SXP-2523 or amikacin in a total dose of 10 or 60 mg/kg, respectively. The test article and control agent were delivered at 2, 4, and 6 hours post infection. Five rats were treated with each drug concentration. One group of five rats were euthanized at initiation of treatment and thigh CFUs were determined (T=Rx). Twenty-four hours post infection; rats were euthanized by $CO_2$ inhalation. The right thigh muscles of the rats were aseptically removed, weighed, homogenized, serially diluted, and plated on BHI medium. The plates were incubated overnight at 37° C. in 5% $CO_2$. CFU per gram of thigh was calculated by enumerating the plated colonies then adjusting for serial dilutions and the weight of the thigh. The following table 8 summarizes the results:

TABLE 8

Rat neutropenic thigh model results against resistant *P. aeruginosa*

| test article | Total Drug Concentration (mg/kg) | n | Log CFU/ thigh | St. Dev. | Change from 24 hr. control | Change from T = Rx controls |
|---|---|---|---|---|---|---|
| T = Rx | — | 5 | 3.49 | 0.46 | — | — |
| 24 hr controls | — | 5 | 6.65 | 0.37 | — | 3.16 |
| SXP-2523 | 10.0 | 5 | 1.71 | 1.13 | −4.94 | −1.78 |
| Amikacin | 60.0 | 5 | 3.92 | 0.72 | −2.73 | 0.43 |

It can be seen that SXP-2523 is effective against amikacin-resistant *P. aeruginosa* in an appropriate animal model.

Synthesis of Examples 1-25 is shown in schematic form in Scheme 1. As shown in Scheme 1, amikacin was first protected with Boc and acetyl groups, then the 5-position was converted to 5-F (or to other substituents $R^5$) as described below. The acetyl protecting groups were then removed with base (e.g. sodium methoxide) and the 6" hydroxyl was tosylated. Displacement with various amines $R^8$-A-NH($R^7$) gave the penultimate product which was cleaved under acidic conditions to provide 5F-amikcin-NH-AHB-R6"-$R^8ANR^7$ analogs:

SCHEME 1

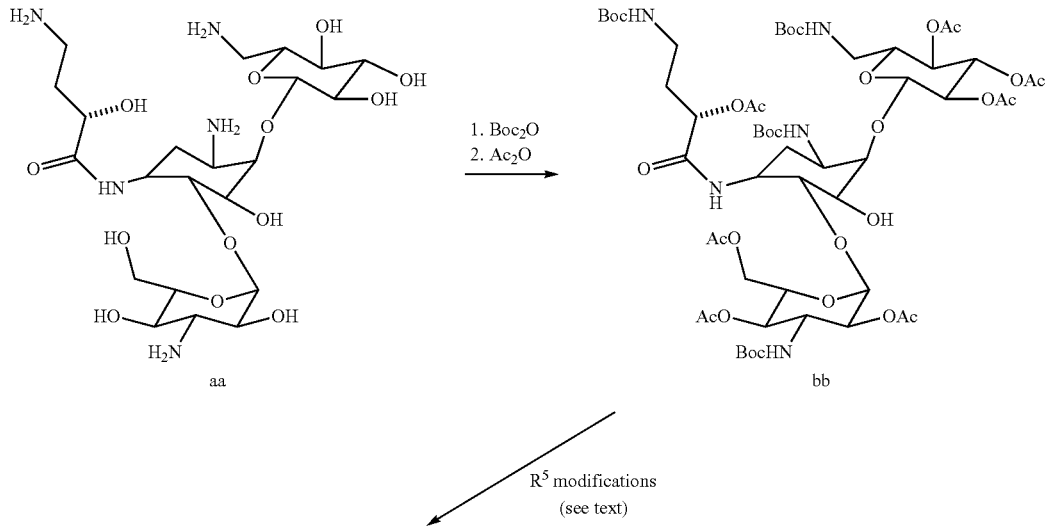

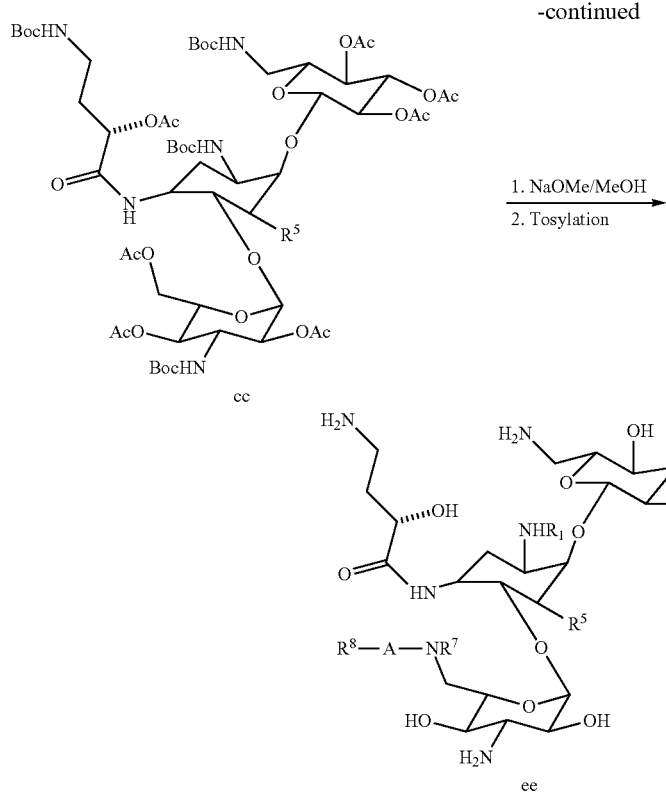

The general procedure for the protection of amines and acetylation of the hydroxyls in the kanamycin aminoglycosides is reported by Shitara et al [Shitara T, Umemura E, Tsuchiya T, Matsuno T *Carbohydrate Research* 276, 75-89 (1995)].

Modification of the R5 hydroxyl group is generally accomplished as follows: For R5-fluoro compounds, the protected aminoglycoside is dissolved in dichloromethane and cooled to −20° C. A solution of deoxo-fluor [bis-(2-methoxyethyl) aminosulfur trifluoride] (DAST) is then added dropwise over 15 min. The reaction is stirred overnight at −20 C and the excess reagent is quenched by the addition of solid $NaHCO_3$. The reaction is worked up by washing the organic layer with aq. $NaHCO_3$, water, sodium hypochlorite solution, and then water. The organic layer is dried and then evaporated to provide the R5-epi-fluoro-5R5-desoxy analogs.

For R5-chloro, bromo and iodo compounds, the protected aminoglycoside is dissolved in dichloromethane (20 ml) and mesitylene sulfonyl chloride (0.25 moles) is added in the presence of catalytic amount of DMAP. The reaction mixture is stirred at room temperature for 5-6 hours and after completion the product is concentrated under vacuum to yield a mesitylene sulfonate intermediate. For chlorides, the intermediate is dissolved in DMF (10 mL) and LiCl (0.5 moles) is added. The reaction is refluxed at 100° C. for 6-8 hours. After completion of the reaction, the product is concentrated under vacuum and suspended in water (20 mL) and extracted with $CH_2Cl_2$ (3×25 mL). The organic layer is washed with brine and dried over anhydrous $Na_2SO_4$ followed by concentration under vacuum to furnish 5-deoxy 5-chloro derivatives. For bromides, the intermediate is dissolved in DMF (10 mL) and NaBr (4 moles) is added. The reaction is refluxed at 100° C. for 18 hours. Work-up of the reaction mixture as above furnishes R5-deoxy-R5-bromo compounds. For iodides, the intermediate is dissolved in DMF (10 mL) and NaI (6 moles) is added. The reaction is refluxed at 100° C. for 18 hours. Work-up of the reaction mixture as above furnishes R5-deoxy-R5-iodo compounds.

For R5 azides and amines, the mesitylene sulfonate intermediate obtained as above is dissolved in DMF (10 mL) and $NaN_3$ (8 moles) is added. The reaction is refluxed at 100° C. for 18 hours. Work-up of the reaction mixture as above furnishes 5-deoxy-R5-azide compounds. The R5-deoxy-R5-azide (500 mg) can be dissolved in dry THF (10 mL) and reduced by adding $LiAlH_4$ in THF (5 mL) at −10° C. The reaction is stirred for 3 hours at room temperature. After the reaction is completed, the reaction mixture is partially concentrated under vacuum and diethyl ether (20 mL) plus dil. HCl (20%, 10 mL) are added with stirring at −10° C. The organic layer is separated and the aqueous layer is washed with excess diethyl ether (2×25 mL). The combined ether layers are washed with brine and died over anhydrous $Na_2SO_4$ followed by concentration under vacuum to furnish R5-deoxy-R5-amine compounds. The amine can be alkylated with the halide of the appropriate ($C_3$-$C_{10}$)carbocycle, ($C_3$-$C_9$)heterocycle, ($C_1$-$C_8$)alkyl($C_3$-$C_{10}$)carbocycle or ($C_1$-$C_8$) alkyl($C_3$-$C_9$)heterocycle. Or the amine can be reacted with an activated ester of an N-Boc-protected aminoacid to provide the compounds in which $R^{50}$ is the deshydroxy residue of the aminoacid.

For compounds in which R5 is an alkyne, the mesitylene sulfonate intermediate can be reacted with a metal salt of the appropriate alkyne, such as sodium acetylide.

General procedure for deprotection of acetyl groups: To a solution of cc (80 mg) in 5 mL of 30% NaOMe in MeOH was added, and the mixture was stirred for overnight. The solution was neutralized with aq HCl and concentrated. The residue was thoroughly washed with water (10 ml) and dried in vacuum at 40° C. to give compounds "dd" (~60%).

General procedure for deprotection of Boc groups: Compound dd (200 mg) was dissolved in dioxane/HCl (10 mL) and stirred at −10° C. for 5-6 hrs. Dioxane was removed under vacuum and the solid obtained was washed with isopropyl ether (2×10 mL) followed by CH₂Cl₂ (2×10 mL) and drying at 40° C. under vacuum furnished the final compounds modified at C—R5 position.

The general synthetic method for incorporation of guanidine groups at all amines of aminoglycosides involves the conditions reported in the literature [Hoshi H, Aburaki S, Iimura S, Yamasaki T, Naito T, Kawaguchi H *The Journal of Antibiotics* 1990, 858-872]. Selective guanidinylation of amines was achieved by reacting protected aminoglycosides with the corresponding equivalents of TfN=C(NHBoc)₂. Thus, for example, if a guanidine is desired at R1, compound "h" of Scheme 2 or compound "n" of Scheme 3 below can be reacted with TfN=C(NHBoc)₂ in the presence of a base such as triethylamine in aqueous solution.

When analogs are desired in which R¹ is not AHB, Scheme 1 can be employed with the appropriate starting material "aa" replacing amikacin. Alternatively, one can follow the procedures of Schemes 2 and 3 below.

Synthesis of Examples 26-29 is shown in schematic form in Schemes 2 and 3. As shown in Scheme 2, tobramycin was first protected with Boc and acetyl groups, then the 5-position was converted to 5-F. The protecting groups were then removed. The 3" and 1 amines were then chelated with Zn(OAc)₂ and the non-chelated amines at 3, 2' and 6' were protected with Boc groups. The 3"-amine was protected as its trifluoroacetamide (TFA amide) and the remaining R1-amine was coupled with various carboxylic acids, including for examples 26-29, (S)-AHB-Boc. The coupling (h→i) may be accomplished by any of the methods well-known in the art of peptide synthesis. Condensing agents for reacting amines with carboxylic acids include carbodiimides of various sorts, mixed anhydrides, EEDQ, HATU, and the like. It is also possible to pre-react the carboxylic acid of the linker with an appropriate leaving group to form an activated ester. Activated esters denote esters which are capable of undergoing a substitution reaction with primary or secondary amines to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters.

The TFA group was then cleaved and replaced with a Boc-group. Tosylation or mesitylation of the R6"-OH followed by displacement with various amines R⁸-A-NH(R⁷) gave the penultimate product which was cleaved under acidic conditions to provide 5F-tobramycin-NH-AHB-R6"-R⁸ANR⁷ analogs:

SCHEME 2

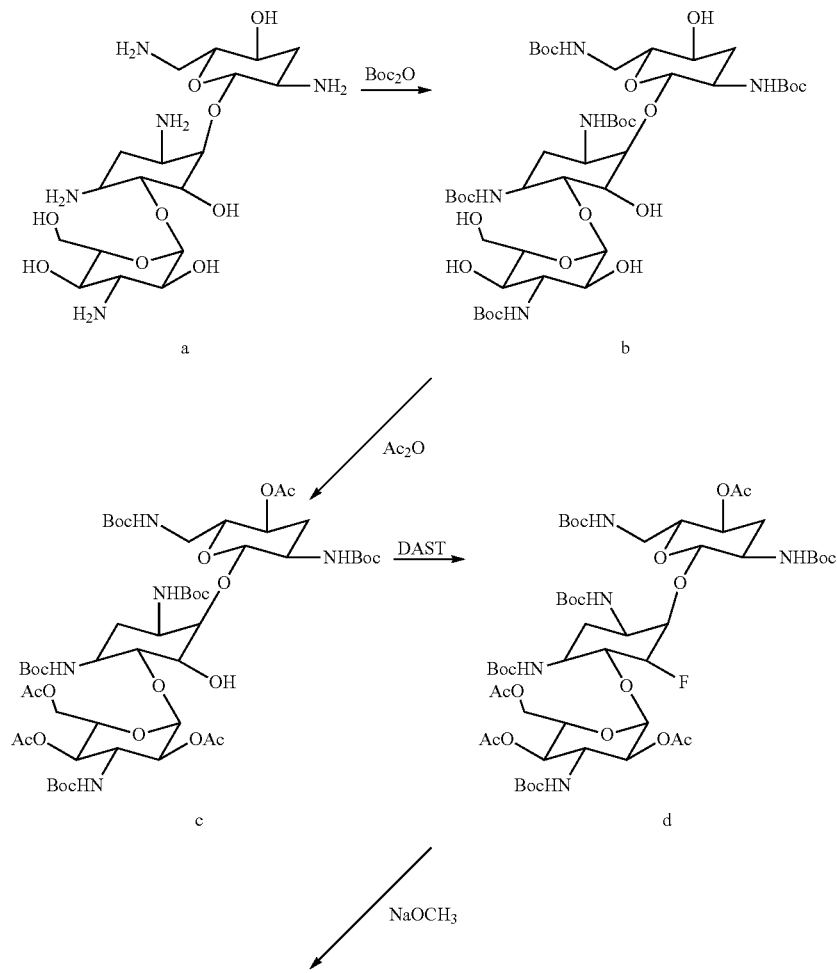

-continued
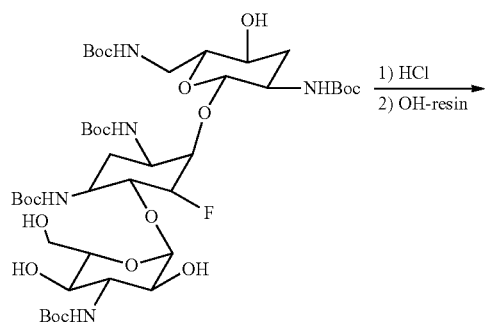
e
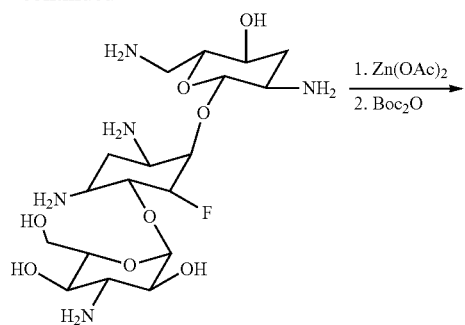
f
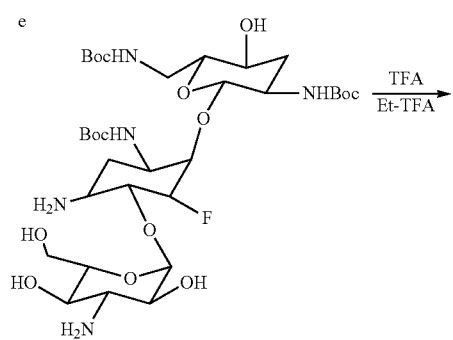
g
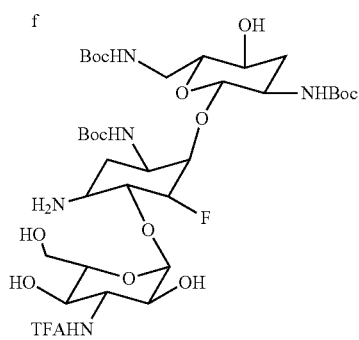
h
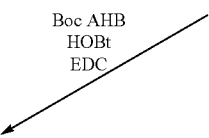
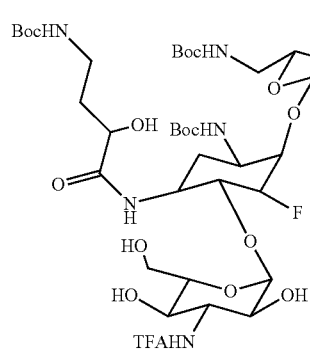
i
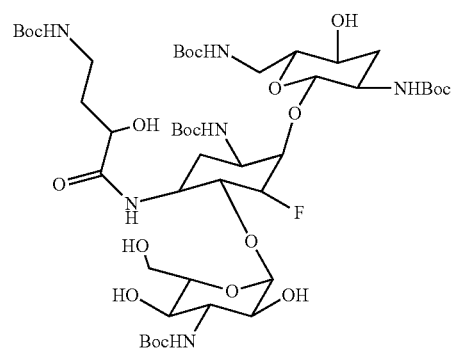
j
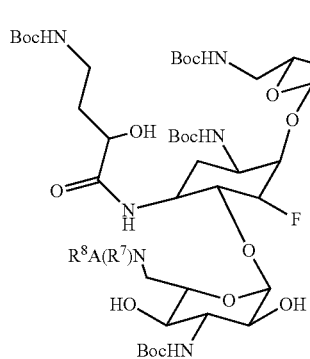
k
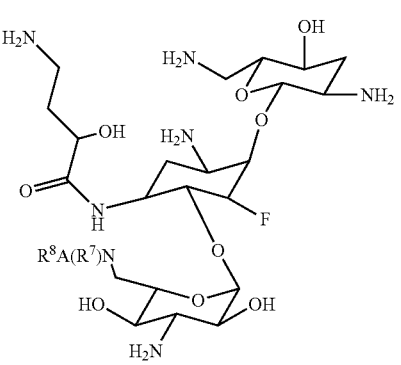
l An alternative route is shown in Scheme 3, wherein tobramycin-zinc complex was reacted with Boc-anhydride and then ethyl trifluoroacetate. The remaining $R^1$ position was then acylated with AHB-Boc. The 3"-TFA was cleaved with base, then protected as a Boc group. The R6"-OH was treated with mesitylene sulfonyl chloride followed by displacement of the mesitylenesulfonate with various amines. The free amines were protected with Boc, followed by selective acylation of the hydroxyl groups, leaving the 5-OH unprotected. The 5-OH was fluorodeoxygenated with DAST [(diethylamino)sulfur trifluoride] or DEOXO-FLUOR® to give the epi-F-desoxy intermediate. This material was then deprotected sequentially, first with $NaOCH_3$ and then with HCl to remove the Boc-groups:

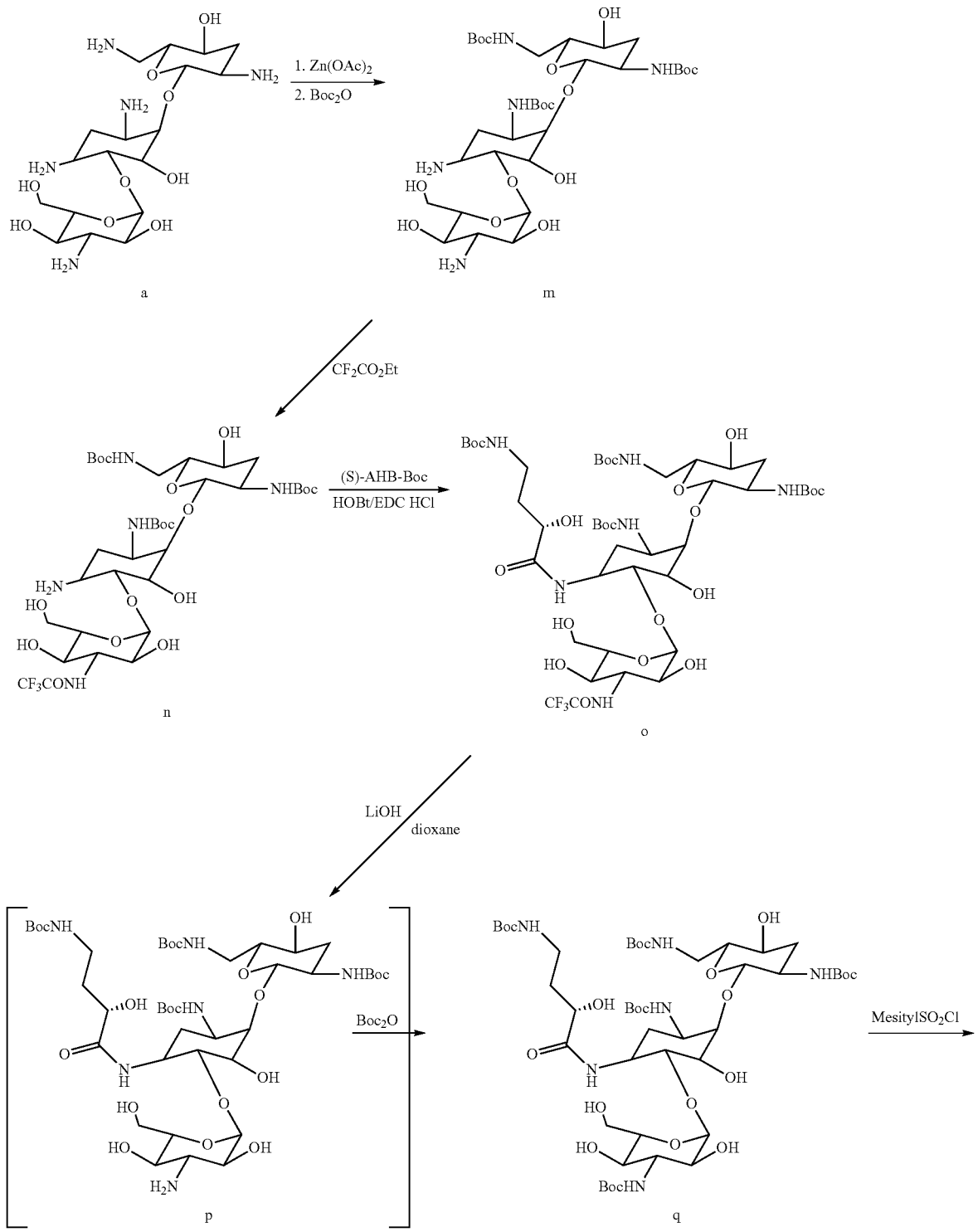

SCHEME 3

-continued

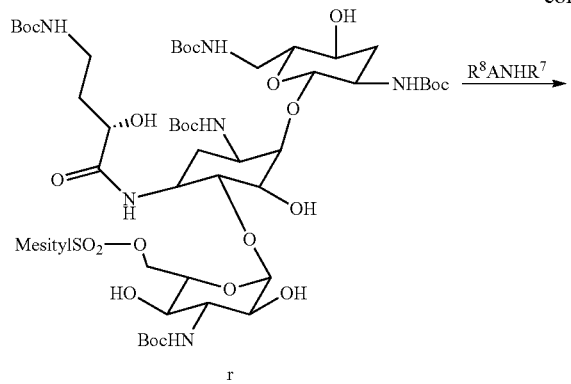
r

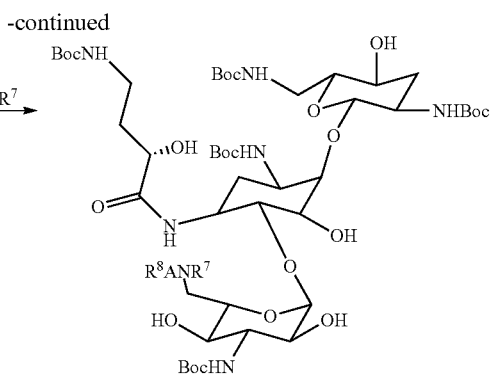
s

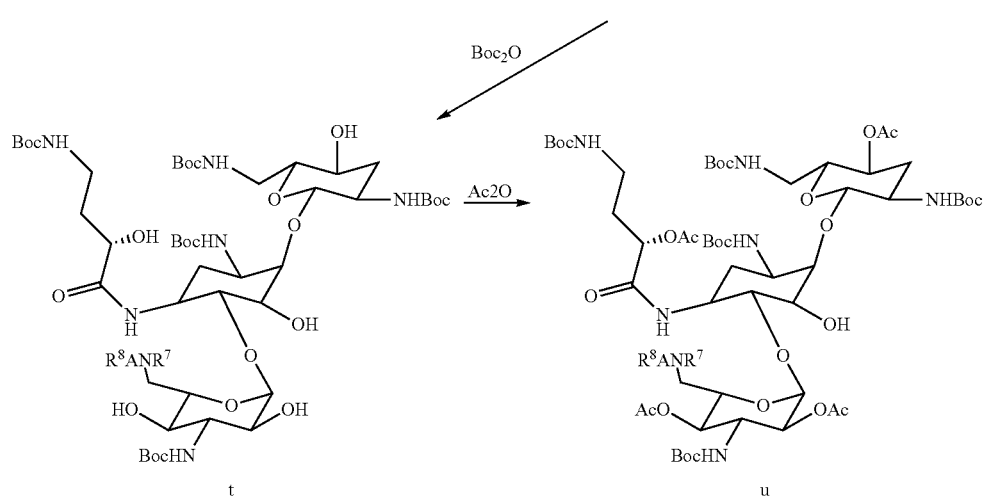
t → u

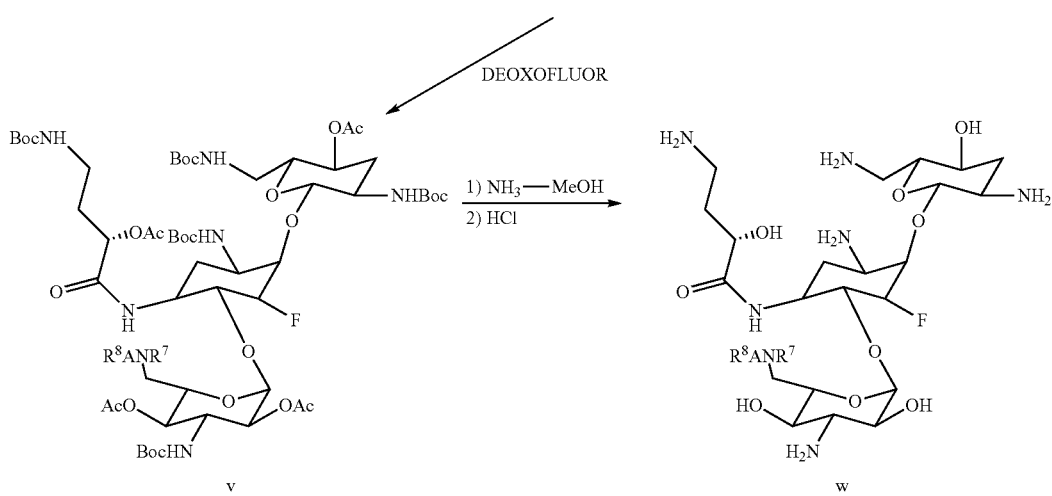
v → w

In a specific example, SXP-2523 was synthesized as follows:

Tetrahydrofuran (250 mL) was added to $Zn(OAc)_2 \cdot 2H_2O$ (29.3 g. 133.8 mmol) in a 500 mL Erlenmeyer flask, swirled for 5 min, and the solid was collected on a fritted glass Buchner funnel and washed with another 250 mL of THF. The solid was completely dried under vacuum for 1 hour at 40° C. The dried $Zn(OAc)_2 \cdot 2H_2O$ and tobramycin free base (25.0 g, 53.5 mmol) were added to a 3 L round-bottom flask and stirred with methanol (350 mL) at room temperature for 2 hours (after 20-25 min clear solution was observed). $Et_3N$ (22.5 mL, 160.5 mmol) was added with stirring, and the initial precipitate that formed dissolved within 30 min to give a clear solution. Boc-anhydride (46.6 g, 214.0 mmol) was added to this solution, and the stirring was continued for 16 h. The progress of the reaction was monitored by LC-MS, which showed about 10% of Tob-$Boc_5$ as the only impurity. The excess Boc-anhydride was quenched by the addition of 28% $NH_4OH$ (3.5 mL) and stirred for 1 hour. Volatiles were removed by rotary evaporation (bath temp 40° C.). The solid residue was dissolved in n-butanol (500 mL) and washed with $NH_4OH$:brine (2:1, 1 L. 3×330 mL), followed by brine (2×330 mL). Then an equal volume of water (500 mL) was added to the butanol layer. The combined water and butanol layers were evaporated using a Genevac$^g$ Rocket Evaporator (45° C., 3 h). The resulting solid was suspended in methanol (~60 mL) and then water (30 mL) was added. Again the combined water and methanol layers were removed using Genevac® Rocket Evaporator (45° C., 18 h). The solid obtained was re-dissolved with methanol, and the insoluble white crystalline solid (NaCl) was discarded by filtration. The methanol layer was concentrated under vacuum to yield 40 g crude product. The major impurity in Tob-Boc$_3$ is Tob-Boc$_5$. HPLC with an evaporative light scattering detector (ELSD) $R_t$ 4.4 min (Phenomenex-C18, 50×3 mm, 4 µm, gradient elution with 95% water (0.1% formic acid) and 100% methanol); LC-MS: m/z 768.33 (M+1) obtained, 767.86 calculated: TLC (Ninhydrin) CH2Cl$_2$:MeOH:28% NH$_4$OH, 8.5:1.0:0.5) $R_f$ 0.25. The impurity was removed from the product by selectively dissolving the product in water. This was achieved by stirring the solid with water (350 mL) for at least 1 hour, followed by filtration through a fritted glass Buchner funnel. This procedure was repeated another three times (total of four washes) until LC-MS showed no product in the residual solid. The combined aqueous layers were concentrated using Genevac Rocket Evaporator (45° C.) to provide 32 g (77.9% yield) of Tob-Boc$_3$ as a pure white solid.

Tob-Boc$_3$ (m) (19.5 g, 25.0 mmol) was co-evaporated with anhydrous DMF (2×50 mL). To a stirred solution of Tob-Boc$_3$ in anhydrous DMF (70 mL) was added ethyl trifluoroacetate (3.62 g, 25.0 mmol) dropwise at 5° C. for 30 min. The mixture was stirred at room temperature for 10 min. The LC-MS of the mixture shows completion of the reaction to Tob-Boc$_3$-TFA (n) with approximately 2-3% Tob-Boc$_3$-TFA$_2$ side product according HPLC/ELSD. (Small-scale reactions at various concentrations of Tob-Boc$_3$ suggest that the amount of Tob-Boc$_3$-TFA$_2$ by-product can be substantially eliminated by performing the reaction at 0.1 M Tob-Boc$_3$ in DMF.) To the reaction mixture were added 31 mL of 1M solution of AHB-Boc in DMF (76.6 mmol), HOBt (4.6 g, 76.6 mmol), 1-ethyl-3-[3-dimethylaminopropyl]carbodiimide hydrochloride (EDC.HCl)(5.8 g, 76.6 mmol) and triethylamine (4.2 mL, 76.6 mmol). The mixture was stirred for 16 hours. LC-MS showed completion of the reaction. Solvents were removed under reduced pressure and to the residue water (400 mL) was added and stirred for 30 minutes. The solid was filtered, placed in a beaker (1 L) and stirred with water (400 mL) for 1 hour and filtered. This was repeated one more time and washed with excess water (400 mL). The final solid was sucked dry on the filter and then dried under vacuum at 40° C. for 1 hour. Tob-Boc$_3$-TFA-AHB-Boc (o) was obtained in 81% yield (21.5 g). HPLC (ELSD) $R_t$ 4.4 min (Phenomenex-C18, 50×3 mm, 4 µm, gradient elution with 95% water (0.1% formic acid) and 100% methanol); LC-MS: m/z 1065.71 (M+1) obtained, 1065.09 calculated; TLC (ninhydrin) (CH$_2$Cl$_2$: MeOH:28% NH$_4$OH, 8.5:1.0:0.5) $R_f$ 0.40.

Thirteen and five-tenths grams (12.7 mmol) of Tob-Boc$_3$-TFA-AHB-Boc (o) was dissolved in 150 mL of dioxane in a round bottomed flask under nitrogen. To this is added a solution of 640 mg of LiOH in 7 mL of water with stirring. The reaction is allowed to stir at room temperature for 2.5 hours and then Boc anhydride 3.3 g (30 mmol) is added. Stirring is continued for a further 2 hours and then the solvent is removed in vacuo. The resulting solid is washed with water by agitating it with 50 mL of water for 15 minutes followed by collection of the solid by filtration. The solid is dried under vacuum overnight to give 6.2 g of 3"-carbamate (q) as free flowing white solid (45% yield.

A round-bottomed flask (oven-dried) equipped with an Argon inlet and a magnetic stir bar was charged with a solution of Tob-N1-AHB(Boc)$_5$ (q) (45.11 g, 42.20 mmol) in dry pyridine (120 mL). The reaction solution was stirred at room temperature and 2-mesitylenesulfonyl chloride (10.08 g, 46.20 mmol) was added. This solution was stirred at room temperature for 20 h, until LC/MS-ELSD showed that it contained at least 90% of the desired product. The major contaminants were 5% remaining starting material and 5% dimesityl compound. Solvents were then removed by rotary evaporation followed by azeotropic removal of pyridine with toluene (3×100 mL). The solid (58.0 g) was washed with water (3×500 mL), to remove pyridinium hydrochloride, filtered to afford a dry powder, which was placed in vacuum oven at 40° C. for 18 h. The solid obtained (45.0 g, 86.5% crude yield) was split into two portions. The first portion (27.0 g) was dry-packed with silica gel, loaded onto a pre-packed 330 g silica gel column and eluted using a Isco Combiflash® $R_f$200 system with a dichloromethane/methanol solvent system (0 to 20% gradient) to afford the desired product (r) Tob-Boc$_4$-N1-AHB-Boc-6"-O-mesylene sulfonate (11.6 g, 43% yield). The remaining 18 g was dry-packed with silica gel and loaded onto a pre-packed 220 g silica gel to afford the desired product (r) (7.6 g, 42.2% yield). Both batches were dissolved in dichloromethane and the solvent was evaporated under reduced pressure to afford a dry powder, which was placed in vacuum oven at 40° C. for 18 hours to yield 17.4 g of Tob-Boc$_4$-N1-AHB-Boc-6"-O-mesitylene sulfonate (33%) $R_t$ 11.7 min (Phenomenex C18, 50×3 mm, 4 µm, gradient elution with 95% water (0.1% formic acid) gradient 100% methanol); LC/MS: m/z 1251.44 (M⁻) observed, 1251.44 calcd. TLC $R_f$ 0.25 (DCM:MeOH=9.5:0.5).

To a stirred solution of Tob-Boc$_4$-N1-AHB-Boc-6"-O-mesitylene sulfonate (r) (17.26 g, 13.8 mmol) in acetonitrile was added 1,3-propanediamine (11.5 mL, 74.12 mmol) at room temperature. The resulting solution was stirred in an oil bath at 70° C. for 18 h, until LC/MS indicated that the reaction was complete. The reaction was worked up by removing the volatiles under reduced pressure and residual 1,3-propanediamine was azeotroped with toluene (3×300 mL) to provide a powder which was dried under high vacuum for 4 h. The crude residue was stirred with NH$_4$OH (1.0 M, 300 mL) for 1 hour then filtered through a sintered glass funnel followed by stirring with deionized water (400 mL). The aqueous suspension was filtered and washed with water (400 mL) until filtrate became neutral to pH paper. The solid was dried under high vacuum at 40° C. for 16 hours to afford a desired product Tob-Boc$_4$-N1-AHB-Boc-6"-propanediamine (s; $R^7$=H, $R^8$=3-aminopropyl) (12.5 g, 87.7% yield). HPLC (ELSD) $R_t$ 7.8 min (Phenomenex C18, 50×3 mm, gradient elution with 95% water (0.1% formic acid) gradient 100% methanol); LC/MS: m/z 1125.44 (M⁺) observed, 1225.30 calc'd. TLC $R_f$ 0.2 (DCM:MeOH:NH$_4$OH=4.95:4.95:0.1).

A round-bottomed flask (oven-dried) equipped with a magnetic stir bar was charged with a solution of Tob-N1-AHB(Boc)$_5$-PDA-Boc (s; $R^7$=H, $R^8$=3-aminopropyl), 12.30 g, 11.0 mmol) 1,4-dixane. The reaction solution was stirred at room temperature and then triethylamine (2.22 mL, 22.0 mmol) followed by (Boc)$_2$O (9.60 g, 44.0 mmol) was added. This solution was stirred at room temperature for 20 h, until LC/MS-ELSD showed completion of the reaction. Solvents were removed by rotary evaporation, and the solid was washed with water (3×500 mL) to remove a trace amount of PDA. The residue was dissolved in dichloromethane (500 mL); the dichloromethane layer was dried over anhyd. MgSO$_4$ for 30 min., filtered and concentrated. The residue was dried overnight under high vacuum to yield a white solid powder Tob-Boc$_4$-N1-AHB-Boc-6"-Boc-propanediamine (t; $R^7$=H, $R^8$=3-Boc-aminopropyl) (14.33 g, 98.4%): HPLC (ELSD) $R_t$ 10.8 min (Phenomenex C18, 50×3 mm, 4 µm, gradient elution with 95% water (0.1% formic acid) gradient 100% methanol); LC/MS: m/z 1125.44 (M+) observed, 1225.30 calc'd. TLC R$_f$ 0.45 (DCM:MeOH=9:1).

1.2 g (0.906 mmol) of Tob-N1-AHB-(Boc)$_5$-PDA (t), was azeotroped with anhydrous pyridine to remove trace amounts of water. It was then taken up in 10 mL of anhydrous pyridine and acetic anhydride (1 mL, 10.5 mmol) was added. The reaction was allowed to stir overnight and then the solvent was removed in vacuo. The resulting material was washed with water and dried under vacuum overnight to give the desired product (u) 1.007 g (77% yield).

0.847 g (0.57 mmol) of the tetraacetyl derivative (u) was dissolved in 10 mL of anhydrous dichloromethane in a round bottom flask under nitrogen. The reaction was cooled to −20° C. and deoxofluor (0.38 g, 1.7 mmol) was added dropwise. The reaction was stirred at −20° C. for 18 h and then quenched at −20° C. by slow addition of 5 mL of 1M aqueous solution of sodium bicarbonate with vigorous stirring. The layers were separated and the aqueous layer was extracted with 3 10 mL portions of dichloromethane. The combined organics were dried over sodium sulfate and condensed in vacuo to give the desired compound (v) as a white solid (351 mg, 41% yield).

0.35 g (0.23 mmol) of the fluorinated derivative (v) was dissolved in methanol and 0.16 mL of a 1.5 N aqueous solution of NaOH was added dropwise with stirring at room temperature. The mixture was allowed to stir at room temperature for 1 hour during which time the reaction turns yellowish. The solvent was removed in vacuo to give a sticky solid. The solid was washed with 10 mL of water and then azeotroped with 25 mL of methanol and twice with 25 mL of toluene and dried under vacuum for 4 hours. The resulting material was carried on to the next reaction without purification.

The crude material from above was dissolved in 0.5 mL of dioxane and cooled to 0° C., at which point the dioxane freezes. The flask was allowed to warm just until the dioxane melted and then cold (0° C.) 4N HCL in dioxane (2 mL, 35 equiv.) was added dropwise with stirring. The mixture was allowed to stir overnight at 0° C. The next day the flask was allowed to warm to room temperature and a solid precipitated out of solution. The solid was purified by recrystallization/precipitation from methanol/tetrahydrofuran to give a pinkish solid (0.192 g).

The final product, SXP2523, was purified by column chromatography using AMBERLITE® CG-50 ion exchange resin (NH$_4^-$ form). A yellow impurity comes off the column first. From the second ELSD peak, initial fractions were contaminated with a possible 5-acetylated, non-fluorinated impurity. These were followed by pure fractions of SXP2523. The last fractions were contaminated with an unknown impurity. Pure fractions were collected, pooled and evaporated using a rotary evaporator to reduce the volume of water and then finally lyophilized to get pure product. The chromatographed product contained 0.5-1 equivalents of HCl (determined using chloride ion titration, Galbraith Labs). It is possible that the eluent, 2N NH$_4$OH, is not a sufficiently strong base to deprotonate the secondary amine in SXP2523.

A 30 mg sample of SXP2523 was dissolved in 140 microliters of D$_2$O for NMR analysis. No pH adjustment was made. All experiments were carried out at a sample temperature of 25 degrees centigrade. The 1D proton, 2D carbon-13 HSQC, HMBC, H2BC, proton 2D DQFCOSY, and TOCSY experiments were run at 600 MHz. The 1D carbon-13, 1D flourine-19 experiments were run at 400 MHz. Table 7 presents the proton and carbon-13 assignments for SXP2523.

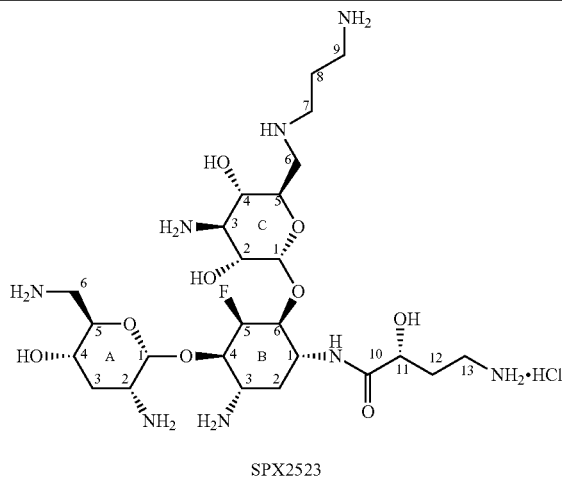

SPX2523

| number | Proton | Carbon-13 |
|---|---|---|
| A1 | 4.85 | 94.27 |
| A2 | 2.84 | 48.51 |
| A3 | 1.53, 1.93 | 35.05 |
| A4 | 3.42 | 65.94 |
| A5 | 3.43 | 72.94 |
| A6 | 2.68, 2.94 | 41.25 |
| B1 | 4.11 | 46.76 |
| B2 | 1.29, 1.91 | 33.61 |
| B3 | 3.11 | 46.42 |
| B4 | 3.45* ($^3$JHF-28 Hz) | 76.91** ($^2$JCF-33 Hz) |
| B5 | 5.10* ($^2$JHF-52 Hz) | 88.78** ($^1$JCF-175 Hz) |
| B6 | 3.80* ($^3$JHF-28 Hz) | 78.24** ($^2$JCF-33 Hz) |
| C1 | 4.89 | 99.26 |
| C2 | 3.26 | 71.31 |
| C3 | 2.84 | 53.68 |
| C4 | 2.99 | 71.54 |
| C5 | 3.68 | 70.90 |
| C6 | 2.56, 2.80 | 49.79 |
| C7 | 2.51 | 46.46 |
| C8 | 1.59 | 28.64 |
| C9 | 2.71 | 38.04 |
| C10 (C') | — | 176.20 |
| C11 | 4.08 | 69.71 |
| C12 | 1.69, 1.86 | 33.86 |
| C13 | 2.77 | 36.86 |

*Peaks show a proton-$^{19}$F coupling as indicated.
**Peaks show a $^{13}$C—$^{19}$F coupling as indicated.
1D fluorine spectrum shows a single peak at −121.2 ppm

The invention claimed is:
1. A compound of formula

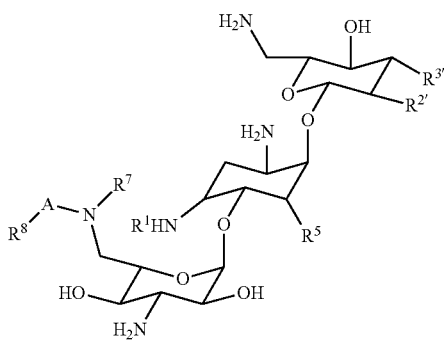

wherein
R$^{2'}$ is chosen from —OH and —NH$_2$;
R$^{3'}$ is chosen from H and —OH;

$R^1$ is chosen from H, —C(=NH)NH$_2$, and —C(=O)R$^{10}$, wherein
  $R^{10}$ is chosen from —(C$_1$-C$_{20}$)alkyl, —(C$_3$-C$_{10}$)carbocycle, —(C$_3$-C$_9$)heterocycle, —(C$_1$-C$_8$)alkyl(C$_3$-C$_{10}$)carbocycle, and —(C$_1$-C$_8$)alkyl(C$_3$-C$_9$)heterocycle wherein
    in said (C$_1$-C$_{20}$)alkyl or in the (C$_1$-C$_8$)alkyl portion of said (C$_1$-C$_8$)alkyl(C$_3$-C$_{10}$)carbocycle or (C$_1$-C$_8$)alkyl(C$_3$-C$_9$)heterocycle, one or two —CH— may be replaced with —N—, two —CH— may be replaced by —C≡C—, and one or two —CH$_2$— may be replaced by —O—, —S—, —SO—, —SO$_2$—, —C≡C—, a (C$_3$-C$_{10}$)carbocycle or a (C$_3$-C$_6$)heterocycle and
    said (C$_1$-C$_{20}$)alkyl, (C$_3$-C$_{10}$)carbocycle, (C$_3$-C$_9$)heterocycle, (C$_1$-C$_8$)alkyl(C$_3$-C$_{10}$)carbocycle, (C$_1$-C$_8$)alkyl(C$_3$-C$_9$)heterocycle may be additionally substituted with from one to three substituents chosen independently from —CH$_3$, —OH, —NH$_2$, —COOH, =O, —NHCONH$_2$, —NHC(=NH)NH$_2$, —CN or halogen;
$R^5$ is chosen from H, halogen, N$_3$, —(C$_1$-C$_4$)alkynyl and —NHR$^{50}$, wherein R$^{50}$ is chosen from H, —(C$_3$-C$_{10}$)carbocycle, —(C$_3$-C$_9$)heterocycle, —(C$_1$-C$_8$)alkyl(C$_3$-C$_{10}$)carbocycle, —(C$_1$-C$_8$)alkyl(C$_3$-C$_9$)heterocycle and the deshydroxy residue of an aminoacid;
$R^7$ is chosen from H, —(C$_1$-C$_6$)alkyl and hydroxy-(C$_1$-C$_6$)alkyl;
$R^8$ is chosen from —(C$_1$-C$_{20}$)alkyl, —(C$_3$-C$_{10}$)carbocycle, —(C$_3$-C$_9$)heterocycle, —(C$_1$-C$_8$)alkyl(C$_3$-C$_{10}$)carbocycle, —(C$_1$-C$_8$)alkyl(C$_3$-C$_9$)heterocycle, —NR$^{80}$R$^{81}$, and —C(=NH)NH$_2$, wherein
  R$^{80}$ and R$^{81}$ are chosen independently from H and —(C$_1$-C$_6$)alkyl;
  in said (C$_1$-C$_{20}$)alkyl or in the (C$_1$-C$_8$)alkyl portion of said (C$_1$-C$_8$)alkyl(C$_3$-C$_{10}$)carbocycle or (C$_1$-C$_8$)alkyl(C$_3$-C$_9$)heterocycle, one or two —CH— may be replaced with —N—, two —CH— may be replaced by —C=C—, and one or two —CH$_2$— may be replaced by —O—, —S—, —SO—, —SO$_2$—, —C≡C—, a (C$_3$-C$_{10}$)carbocycle or a (C$_3$-C$_6$)heterocycle; and
  said (C$_1$-C$_{20}$)alkyl, (C$_3$-C$_{10}$)carbocycle, (C$_3$-C$_9$)heterocycle, (C$_1$-C$_8$)alkyl(C$_3$-C$_{10}$)carbocycle, (C$_1$-C$_8$)alkyl(C$_3$-C$_9$)heterocycle may be additionally substituted with from one to three substituents chosen independently from —CH$_3$, —CH$_2$CH$_3$, —OH, —CH$_2$OH, —NH$_2$, —CH$_2$NH$_2$, —COOH, =O, —NHCONH$_2$, —NHC(=NH)NH$_2$, —CN and halogen;
or
$R^7$ and R$^8$A, taken together with the nitrogen to which they are attached, form a (C$_3$-C$_9$)heterocycle, said (C$_3$-C$_9$)heterocycle optionally substituted with from one to three substituents chosen independently from —CH$_3$, —CH$_2$CH$_3$, —OH, —CH$_2$OH, —NH$_2$, —CH$_2$NH$_2$, —COOH, =O, —NHCONH$_2$, —NHC(=NH)NH$_2$, —CN and halogen; and
A is chosen from a direct bond, —(C=O)—, —C(=O)O—, —NH(C=O)—, —(C=O)NH—, —NH(C=O)NH—, —(C=S)NH—, —NH(C=S)—, and —NH(C=S)NH—.

2. A compound according to claim 1 wherein R$^1$ is —C(=O)R$^{10}$.

3. A compound according to claim 2 wherein R$^{10}$ is chosen from —(C$_1$-C$_{15}$)alkyl, —(C$_3$-C$_6$)carbocycle, —(C$_3$-C$_5$)heterocycle, —(C$_1$-C$_3$)alkyl(C$_3$-C$_6$)carbocycle and —(C$_1$-C$_3$)alkyl(C$_3$-C$_5$)heterocycle, wherein
  in said (C$_1$-C$_{15}$)alkyl or in the (C$_1$-C$_3$)alkyl portion of said (C$_1$-C$_3$)alkyl(C$_3$-C$_6$)carbocycle or (C$_1$-C$_3$)alkyl(C$_3$-C$_5$)heterocycle, one or two —CH— may be replaced with —N—, two —CH— may be replaced by —C=C—, and one or two —CH$_2$— may be replaced by —O—, —S—, —SO—, —SO$_2$—, —C≡C—, a (C$_3$-C$_{10}$)carbocycle or a (C$_3$-C$_6$)heterocycle and
  said (C$_1$-C$_{15}$)alkyl, (C$_3$-C$_6$)carbocycle, (C$_3$-C$_5$)heterocycle, (C$_1$-C$_3$)alkyl(C$_3$-C$_6$)carbocycle or (C$_1$-C$_3$)alkyl(C$_3$-C$_5$)heterocycle, may be additionally substituted with from one to three substituents chosen independently from —CH$_3$, —OH, —NH$_2$, —COOH, =O, —NHCONH$_2$, —NHC(=NH)NH$_2$, —CN or halogen.

4. A compound according to claim 3 wherein R$^{10}$ is chosen from optionally substituted cyclopropyl, cyclobutyl, cyclopentyl, cyclohexyl, phenyl, pyrrole, imidazole, furan, tetrahydrofuran, piperidine, imidazolylmethyl, —(C$_1$-C$_{10}$)alkyl, and —(C$_1$-C$_{10}$)alkyl in which one or two —CH— may be replaced with —N—, two —CH— may be replaced by —C=C—, and one or two —CH$_2$— may be replaced by —O—, —S—, —SO—, —SO$_2$— or —C≡C.

5. A compound according to claim 3 wherein R$^{10}$ is chosen from
a. the descarboxy residue of a natural α-amino acid;
b. —CH(R$^{11}$)—(CH$_2$)$_n$—NHR$^{12}$, wherein
  n is zero to six;
  R$^{11}$ is —OH or —NH$_2$, and
  R$^{12}$ is chosen from H, —(C$_1$-C$_6$)haloalkyl, —C(=NH)NH$_2$, and the deshydroxy residue of a natural α-amino acid; and
c. —(CH$_2$)$_n$—R$^{13}$, wherein R$^{13}$ is chosen —OH, optionally substituted phenyl and optionally substituted 5- or 6-membered ring heterocycle.

6. A compound according to claim 5 wherein —(C=O)R$^{10}$ is 4-amino-2-hydroxybutyryl.

7. A compound according to claim 1 wherein R$^5$ is chosen from H, halogen, N$_3$ and —NHR$^{50}$, wherein R$^{50}$ is chosen from H, cyclopropyl, cyclopropylmethyl, pyrrolidinyl, and the deshydroxy residue of citrulline or serine.

8. A compound according to claim 7 wherein R$^5$ is fluorine.

9. A compound according to claim 1 wherein A is a direct bond and R$^7$ and R$^8$ are chosen independently from —(C$_1$-C$_6$)alkyl and hydroxy-(C$_1$-C$_6$)alkyl.

10. A compound according to claim 1 wherein
R$^7$ is H;
A is chosen from a direct bond, —(C=O)—, —C(=O)O—, and —NH(C=O)—; and
R$^8$ is chosen from —(C$_1$-C$_{15}$)alkyl, —(C$_3$-C$_{10}$)carbocycle, —(C$_3$-C$_6$)heterocycle, —(C$_1$-C$_3$)alkyl(C$_3$-C$_6$)carbocycle, —(C$_1$-C$_3$)alkyl(C$_3$-C$_6$)heterocycle, —N(CH$_3$)$_2$ —NH$_2$, and —C(=NH)NH$_2$, wherein
  in said (C$_1$-C$_{15}$)alkyl or in the (C$_1$-C$_3$)alkyl portion of said (C$_1$-C$_3$)alkyl(C$_3$-C$_6$)carbocycle or (C$_1$-C$_3$)alkyl(C$_3$-C$_6$)heterocycle, one or two —CH— may be replaced with —N—, two —CH— may be replaced by —C=C—, and one or two —CH$_2$— may be replaced by —O—, —SO$_2$—, —C≡C—, a (C$_5$-C$_6$)carbocycle or a (C$_3$-C$_4$)heterocycle and
  said (C$_1$-C$_{15}$)alkyl, (C$_3$-C$_{10}$)carbocycle, (C$_3$-C$_6$)heterocycle, (C$_1$-C$_3$)alkyl(C$_3$-C$_6$)carbocycle, (C$_1$-C$_3$)alkyl(C$_3$-C$_6$)heterocycle may be additionally substituted with from one to three substituents chosen independently from —CH$_3$, —CH$_2$CH$_3$, —OH, —CH$_2$OH, —NH$_2$, —COOH, =O, —NHCONH$_2$, —NHC(=NH)NH$_2$, and halogen.

11. A compound according to claim 10 wherein A is a direct bond and $R^8$ is chosen from $-N(CH_3)_2$, $-NH_2$, and $-C(=NH)NH_2$.

12. A compound according to claim 10 wherein A is chosen from a direct bond and $-(C=O)-$, and $R^8$ is chosen from $-(C_1-C_{15})$alkyl, $-(C_3-C_{10})$carbocycle, $-(C_3-C_6)$heterocycle, $-(C_1-C_3)$alkyl$(C_3-C_6)$carbocycle, and $-(C_1-C_3)$alkyl$(C_3-C_6)$heterocycle, and wherein said $(C_1-C_{15})$alkyl, $(C_3-C_{10})$carbocycle, $(C_3-C_6)$heterocycle, $(C_1-C_3)$alkyl$(C_3-C_6)$carbocycle, $(C_1-C_3)$alkyl$(C_3-C_6)$heterocycle may be additionally substituted with from one to three substituents chosen independently from $-CH_3$, $-CH_2CH_3$, $-OH$, $-CH_2OH$, $-NH_2$, $-COOH$, $=O$, $-NHCONH_2$, $-NHC(=NH)NH_2$, and halogen.

13. A compound according to claim 10 wherein $R^8$ is $-(C_1-C_{15})$alkyl wherein
one or two $-CH-$ may be replaced with $-N-$, two $-CH-$ may be replaced by $-C=C-$, and one or two $-CH_2-$ may be replaced by $-O-$, $-SO_2-$, $-C\equiv C-$, cyclopentyl, cyclohexyl, furan or dioxole and wherein said $(C_1-C_{15})$alkyl or replaced $(C_1-C_{15})$alkyl may additionally be substituted with from one to three substituents chosen independently from $-CH_3$, $-CH_2CH_3$, $-OH$, $-CH_2OH$, $-NH_2$, $-COOH$, $=O$, $-NHCONH_2$, $-NHC(=NH)NH_2$, and halogen.

14. A compound according to claim 13 wherein A is a direct bond and $R^8$ is $-(C_1-C_6)$alkyl additionally substituted with one to or two substituents chosen independently from $-OH$, $-NH_2$, and $-NHC(=NH)NH_2$.

15. A compound according to claim 14 wherein $R^8$ is aminopropyl.

16. A compound according to claim 1 wherein $R^7$ and $R^8A$, taken together with the nitrogen to which they are attached, form a $(C_3-C_6)$heterocycle, said $(C_3-C_6)$heterocycle optionally substituted with from one to three substituents chosen independently from $-CH_3$, $-CH_2CH_3$, $-OH$, $-CH_2OH$, $-NH_2$, $-CH_2NH_2$, $-COOH$, $=O$, $-NHCONH_2$, $-NHC(=NH)NH_2$, $-CN$ and halogen.

17. A compound according to claim 16 wherein $R^7$ and $R^8A$, taken together with the nitrogen to which they are attached, form a piperidine, piperazine, tetrahydropyrimidine or pyrrolidine, optionally substituted with $-CH_3$, $-CH_2CH_3$, $-OH$, $-CH_2OH$, $-NH_2$, $-CH_2NH_2$, $-COOH$, $=O$, $-NHCONH_2$, $-NHC(=NH)NH_2$, $-CN$ or halogen.

18. A compound according to claim 2 wherein:
$R^{10}$ is chosen from optionally substituted cyclopropyl, cyclobutyl, cyclopentyl, cyclohexyl, phenyl, pyrrole, imidazole, furan, tetrahydrofuran, piperidine, imidazolylmethyl, $-(C_1-C_{10})$alkyl, and $-(C_1-C_{10})$alkyl in which one or two $-CH-$ may be replaced with $-N-$, two $-CH-$ may be replaced by $-C=C-$, and one or two $-CH_2-$ may be replaced by $-O-$, $-S-$, $-SO-$, $-SO_2-$ or $-C\equiv C-$; or
$R^{10}$ is chosen from
a. the descarboxy residue of a natural α-amino acid;
b. $-CH(R^{11})-(CH_2)_n-NHR^{12}$, wherein
n is zero to six;
$R^{11}$ is $-OH$ or $-NH_2$, and
$R^{12}$ is chosen from H, $-(C_1-C_6)$haloalkyl, $-C(=NH)NH_2$, and the deshydroxy residue of a natural α-amino acid; and
c. $-(CH_2)_n-R^{13}$, wherein $R^{13}$ is chosen from $-OH$, optionally substituted phenyl and optionally substituted 5- or 6-membered ring heterocycle;
A is chosen from a direct bond and $-(C=O)-$; and
$R^8$ is chosen from $-(C_1-C_{15})$alkyl, $-(C_3-C_{10})$carbocycle, $-(C_3-C_6)$heterocycle, $-(C_1-C_3)$alkyl$(C_3-C_6)$carbocycle, and $-(C_1-C_3)$alkyl$(C_3-C_6)$heterocycle, and wherein said $(C_1-C_{15})$alkyl, $(C_3-C_{10})$carbocycle, $(C_3-C_6)$heterocycle, $(C_1-C_3)$alkyl$(C_3-C_6)$carbocycle, $(C_1-C_3)$alkyl$(C_3-C_6)$heterocycle may be additionally substituted with from one to three substituents chosen independently from $-CH_3$, $-CH_2CH_3$, $-OH$, $-CH_2OH$, $-NH_2$, $-COOH$, $=O$, $-NHCONH_2$, $-NHC(=NH)NH_2$, and halogen.

19. A compound according to claim 1 wherein $R^5$ is chosen from H, fluorine, $N_3$ and $-NHR^{50}$, wherein $R^{50}$ is chosen from H, cyclopropyl, cyclopropylmethyl, pyrrolidinyl, and the deshydroxy residue of citrulline or serine.

20. A compound according to claim 18 wherein $R^5$ is chosen from H, fluorine, $N_3$ and $-NHR^{50}$, wherein $R^{50}$ is chosen from H, cyclopropyl, cyclopropylmethyl, pyrrolidinyl, and the deshydroxy residue of citrulline or serine.

21. A compound according to claim 15 wherein $R^5$ is fluorine.

22. A compound according to claim 21 wherein $-(C=O)R^{10}$ is 4-amino-2-hydroxybutyryl.

23. A compound according to claim 1 wherein $R^{2'}$ is $-NH_2$ and $R^{3'}$ is H.

24. A method of treating a mammal suffering from a bacterial infection, said method comprising administering a therapeutically effective amount of a compound according to claim 1.

25. A pharmaceutical composition comprising a pharmaceutically acceptable carrier and a compound according to claim 1.

* * * * *